(12) United States Patent
Caneppele et al.

(10) Patent No.: US 12,268,576 B2
(45) Date of Patent: Apr. 8, 2025

(54) EXTENSIBLE DRESSINGS

(71) Applicant: Johnson & Johnson Consumer Inc., Skillman, NJ (US)

(72) Inventors: Leonardo Caneppele, São José dos Campos (BR); Andre Narcizo, São José dos Campos (BR); Paulo Cesar de Godoy Oriani, Sao Paulo (BR); Carmine Rizzo, Port St. Lucie, FL (US); Andre Luiz Santos, São José dos Campos (BR)

(73) Assignee: Kenvue Brands LLC, Summit, NJ (US)

( * ) Notice: Subject to any disclaimer, the term of this patent is extended or adjusted under 35 U.S.C. 154(b) by 278 days.

(21) Appl. No.: 15/950,341

(22) Filed: Apr. 11, 2018

(65) Prior Publication Data
US 2018/0289552 A1  Oct. 11, 2018

Related U.S. Application Data

(60) Provisional application No. 62/483,989, filed on Apr. 11, 2017.

(51) Int. Cl.
*A61F 13/00* (2024.01)
*A61F 13/01* (2024.01)
(Continued)

(52) U.S. Cl.
CPC ........ *A61F 13/00* (2013.01); *A61F 13/01025* (2024.01); *A61F 13/01038* (2024.01); *A61F 13/023* (2013.01); *A61F 13/0243* (2013.01); *A61F 13/0266* (2013.01); *A61L 15/26* (2013.01); *A61F 2013/00595* (2013.01); *A61F 2013/00604* (2013.01); *A61F 2013/00655* (2013.01); *A61F 13/0206* (2013.01)

(58) Field of Classification Search
CPC ................ A61F 13/00; A61F 13/00038; A61F 13/00025; A61F 13/023; A61F 13/0243; A61F 13/0266; A61F 13/0206; A61F 2013/00655; A61F 2013/00604; A61F 2013/00595; A61F 13/01021; A61F 13/01029; A61F 13/01038
See application file for complete search history.

(56) References Cited

U.S. PATENT DOCUMENTS

D65,736   S   10/1924  Groman
2,096,564 A   10/1937  Scholl
(Continued)

FOREIGN PATENT DOCUMENTS

EP    136594       12/1988
EP    0 300 815 A2  1/1989
(Continued)

OTHER PUBLICATIONS

Gabriel, Lester: "Chapter 1: History and Physical Chemistry of HDPE". (Year: 2008).*
(Continued)

*Primary Examiner* — Rachael E Bredefeld
*Assistant Examiner* — Seth R. Brown

(57) ABSTRACT

The present invention relates to dressings such as bandages or tapes having improved extensibility and conformability to human skin and joints.

19 Claims, 9 Drawing Sheets

(51) Int. Cl.
*A61F 13/02* (2024.01)
*A61F 13/0206* (2024.01)
*A61L 15/26* (2006.01)

(56) References Cited

U.S. PATENT DOCUMENTS

| | | | |
|---|---|---|---|
| D127,402 S | 11/1940 | Schwartz | |
| D183,699 S | 10/1958 | Martin | |
| 2,877,765 A | 3/1959 | Bunyan | |
| 2,905,174 A | 9/1959 | Smith | |
| 2,924,331 A | 2/1960 | Hoey | |
| 2,946,435 A | 7/1960 | Schladermundt et al. | |
| 3,024,786 A | 3/1962 | Fuzak | |
| 3,655,501 A * | 4/1972 | Tesch | B32B 27/00 428/137 |
| 3,728,206 A | 4/1973 | Buese | |
| 4,541,426 A | 9/1985 | Webster | |
| 4,545,339 A | 10/1985 | Kubach | |
| 4,612,230 A * | 9/1986 | Liland | A61B 17/085 428/167 |
| 4,999,235 A * | 3/1991 | Lunn | A61L 15/26 442/151 |
| 5,158,555 A | 10/1992 | Porzilli | |
| 5,188,124 A | 2/1993 | Feret | |
| 5,252,066 A | 10/1993 | Fairhurst | |
| 5,256,062 A | 10/1993 | Griott | |
| 5,267,952 A | 12/1993 | Gardner | |
| D383,211 S | 9/1997 | Dunshee et al. | |
| 5,667,864 A | 9/1997 | Landoll | |
| D387,169 S | 12/1997 | Dunshee et al. | |
| D389,244 S | 1/1998 | Dunshee et al. | |
| 5,709,651 A * | 1/1998 | Ward | A61F 13/023 602/42 |
| D391,639 S | 3/1998 | Dunshee et al. | |
| D395,780 S | 7/1998 | Denney et al. | |
| D402,371 S | 12/1998 | Haynes et al. | |
| D404,136 S | 1/1999 | Dunshee et al. | |
| D407,160 S | 3/1999 | Dunshee et al. | |
| D410,087 S | 5/1999 | Dunshee et al. | |
| 5,919,411 A | 7/1999 | Rezai et al. | |
| 5,964,742 A | 10/1999 | McCormack et al. | |
| D422,151 S | 4/2000 | Hwang et al. | |
| 6,162,960 A | 12/2000 | Klein | |
| 6,297,420 B1 | 10/2001 | Heincke | |
| D452,324 S | 12/2001 | Brogden et al. | |
| D470,592 S | 2/2003 | Dunshee | |
| D471,631 S | 3/2003 | Dunshee et al. | |
| D471,632 S | 3/2003 | Dunshee et al. | |
| D495,419 S | 8/2004 | Dunshee | |
| D511,006 S | 10/2005 | Dodd et al. | |
| D514,703 S | 2/2006 | Palomino, Jr. | |
| D573,260 S | 7/2008 | Dunshee | |
| D578,651 S | 10/2008 | Dunshee | |
| D582,608 S | 12/2008 | Palmer | |
| D605,816 S | 12/2009 | Holden et al. | |
| D636,607 S | 4/2011 | Withers | |
| 7,982,087 B2 | 7/2011 | Greener | |
| 8,236,083 B2 | 8/2012 | Garcia et al. | |
| 8,283,514 B2 | 10/2012 | Baschnagel | |
| D672,154 S | 12/2012 | Huss et al. | |
| 8,387,497 B2 | 3/2013 | Raidel et al. | |
| D683,035 S | 5/2013 | Dunshee et al. | |
| D688,882 S | 9/2013 | Rhodes et al. | |
| D692,673 S | 11/2013 | Rhodes, III et al. | |
| D693,130 S | 11/2013 | Rhodes, III et al. | |
| D694,892 S | 12/2013 | Chan et al. | |
| 8,613,993 B2 * | 12/2013 | Kuchar | D04D 9/00 229/87.01 |
| D696,869 S | 1/2014 | Rhodes, III et al. | |
| D697,216 S | 1/2014 | Chan et al. | |
| 8,680,360 B2 | 3/2014 | Greener et al. | |
| D707,829 S | 6/2014 | Chan et al. | |
| D708,751 S | 7/2014 | Chan et al. | |
| D712,546 S | 9/2014 | Igwebuike et al. | |
| D714,560 S | 10/2014 | Xu et al. | |
| D723,175 S | 2/2015 | Igwebuike et al. | |
| D728,803 S | 5/2015 | Sinda et al. | |
| D741,498 S | 10/2015 | Kawahara et al. | |
| D745,688 S | 12/2015 | Chan et al. | |
| D745,689 S | 12/2015 | Chan et al. | |
| D745,690 S | 12/2015 | Devenish et al. | |
| D746,479 S | 12/2015 | Arefleg | |
| D746,996 S | 1/2016 | Karlsson et al. | |
| D748,921 S | 2/2016 | Romano, III et al. | |
| D749,210 S | 2/2016 | Appelbaum et al. | |
| 9,308,115 B2 | 4/2016 | Quinn | |
| D756,668 S | 5/2016 | Blythe et al. | |
| D757,950 S | 5/2016 | Karlsson et al. | |
| D765,993 S | 9/2016 | Palzewicz | |
| D770,631 S | 11/2016 | Green | |
| D773,194 S | 12/2016 | Hurley et al. | |
| 9,511,215 B2 | 12/2016 | Skiba | |
| D777,456 S | 1/2017 | Azeredo et al. | |
| 9,533,809 B2 * | 1/2017 | Kuchar | B65D 65/38 |
| D789,616 S | 6/2017 | Votel et al. | |
| D790,071 S | 6/2017 | Ahsani et al. | |
| 9,820,888 B2 | 11/2017 | Greener et al. | |
| D807,518 S | 1/2018 | Gildersleeve | |
| D823,608 S | 7/2018 | Stephani et al. | |
| D825,202 S | 8/2018 | Stephani et al. | |
| D840,026 S | 2/2019 | Candy | |
| 10,219,953 B2 | 3/2019 | Dewitt et al. | |
| D845,647 S | 4/2019 | Zhu et al. | |
| D848,004 S | 5/2019 | Del Rossi et al. | |
| 10,299,966 B2 | 5/2019 | Pigg | |
| D851,776 S | 6/2019 | Weinstein | |
| D851,944 S | 6/2019 | Toelke et al. | |
| D851,945 S | 6/2019 | Toelke et al. | |
| D851,946 S | 6/2019 | Toelke et al. | |
| D851,947 S | 6/2019 | Toelke et al. | |
| 10,307,587 B2 | 6/2019 | King et al. | |
| D852,512 S | 7/2019 | Toelke et al. | |
| D852,513 S | 7/2019 | Toelke et al. | |
| D852,514 S | 7/2019 | Toelke et al. | |
| D856,005 S | 8/2019 | Chaturvedi | |
| 10,442,574 B2 * | 10/2019 | Kuchar | B65D 27/005 |
| 10,470,935 B2 * | 11/2019 | Quintero | A61F 13/0243 |
| D878,608 S | 3/2020 | Tapper et al. | |
| D879,972 S | 3/2020 | Caneppele et al. | |
| D879,973 S | 3/2020 | Caneppele et al. | |
| D879,974 S | 3/2020 | Caneppele et al. | |
| D879,975 S | 3/2020 | Caneppele et al. | |
| D880,705 S | 4/2020 | Caneppele et al. | |
| D887,563 S | 6/2020 | Caneppele et al. | |
| D887,564 S | 6/2020 | Caneppele et al. | |
| D890,352 S | 7/2020 | Dechow | |
| D895,813 S | 9/2020 | Hicken et al. | |
| D900,486 S | 11/2020 | Steenblock et al. | |
| D901,801 S | 11/2020 | Aragon et al. | |
| D904,624 S | 12/2020 | Del Rossi | |
| D911,537 S | 2/2021 | Weinstein | |
| D913,507 S | 3/2021 | Caneppele et al. | |
| D918,398 S | 5/2021 | Caneppele et al. | |
| D919,821 S | 5/2021 | Fosler et al. | |
| D923,801 S | 6/2021 | Lee | |
| D927,860 S | 8/2021 | Jacob et al. | |
| D931,472 S | 9/2021 | Toth et al. | |
| D942,155 S | 2/2022 | McClain et al. | |
| D942,156 S | 2/2022 | McClain et al. | |
| D942,759 S | 2/2022 | McClain et al. | |
| 2002/0156410 A1 | 10/2002 | Lawry | |
| 2004/0002676 A1 | 1/2004 | Siegwart et al. | |
| 2004/0049144 A1 | 3/2004 | Cea | |
| 2006/0057369 A1 | 3/2006 | Hilfenhaus et al. | |
| 2010/0016771 A1 | 1/2010 | Arbesman et al. | |
| 2010/0100022 A1 * | 4/2010 | Greener | A61F 13/00995 83/13 |
| 2010/0179463 A1 * | 7/2010 | Greener | B26F 1/02 83/13 |
| 2010/0210988 A1 | 8/2010 | Dallison et al. | |
| 2010/0247844 A1 | 9/2010 | Curro et al. | |
| 2011/0092874 A1 | 4/2011 | Baschnagel | |
| 2012/0041402 A1 | 2/2012 | Greener | |
| 2012/0220973 A1 | 8/2012 | Chan et al. | |

(56) References Cited

U.S. PATENT DOCUMENTS

| | | | |
|---|---|---|---|
| 2012/0220974 A1 | 8/2012 | Chan et al. | |
| 2012/0220975 A1 | 8/2012 | Chan et al. | |
| 2012/0247487 A1* | 10/2012 | Llinas | A61B 17/02 128/849 |
| 2013/0282049 A1* | 10/2013 | Peterson | A61F 5/08 606/204.45 |
| 2014/0094730 A1 | 4/2014 | Greener et al. | |
| 2016/0058998 A1 | 3/2016 | Skiba et al. | |
| 2017/0087027 A1 | 3/2017 | Coffey et al. | |
| 2018/0289553 A1 | 10/2018 | Caneppele et al. | |
| 2018/0289559 A1 | 10/2018 | Caneppele et al. | |
| 2019/0099297 A1 | 4/2019 | Cettina et al. | |
| 2020/0246193 A1 | 8/2020 | Wurapa | |

FOREIGN PATENT DOCUMENTS

| | | |
|---|---|---|
| EP | 3085344 | 10/2016 |
| GB | 821959 | 10/1959 |
| JP | S 51-25503 A | 3/1976 |
| JP | H 10-118174 A | 5/1998 |
| JP | 200687488 A | 4/2006 |
| JP | 2010-075437 A | 4/2010 |
| WO | 2010/097570 | 9/2010 |
| WO | 2014/149718 | 9/2014 |
| WO | WO 2016/030047 A1 | 3/2016 |
| WO | 2016/081708 | 5/2016 |

OTHER PUBLICATIONS

Amazon. Band-Aid Brand Tru-Stay Sheer Strips Adhesive Bandages for First Aid Review by "k1dpr". Mar. 7, 2017. https://www.amazon.com/dp/B0009STDOW/ref=psdc_3762721_t4_B00B6A6Y9E (Year 2017).

"'Band-Aid' wound power pad for elbow and knee protection", published in "'Protection series', new for 'Band-Aid' would power pad, effectively protecting shallow and broad wound", dated Mar. 16, 2010, stored in and published from Internet Archive, run by the US non-profit corporation Internet Archive (output date: May 12, 2014). Internet Archive URL: https://web.archive.org/web/20100316073304/http://www.jnj.co.jp/group/press/2009/0309/index.html.

Democrat and Chronicle. Old-school Snake game is making a comeback by WUSA 9 Staff. May 7, 2015. https://www.democratandchronicle.com/story/news/local/2015/05/07/snake-game-makes-comeback/70938102/ (Year 2015).

Douglas Flynt. Accurate Ellipses. Aug. 8, 2011; Oct. 11, 2011. http://douglasflynt.blogspot.com/2011/08/accurate-ellipses.html (Year 2011).

IStock Photo. Seamless pattern with zigzag and triple X shaped line segments stock illustration. Jul. 2, 2018. https://www.istockphoto.com/vector/seamless-pattern-with-zigzag-and-triple-x-shaped-line-segments-gm990118502-268386144 (Year 2018).

Nancy Cartwright. Nancy Cartwright Takes Over as "Chuckie" on The Rugrats. Jul. 2, 2002. https://nancycartwright.com.news/nancy-takes-over-as-chuckie-on-the-rugrats/ (Year 2002).

The Next Plate. Creative Cake Cutting idea. Oct. 27, 2010. https://thenextplate.tumbir.com/ (Year 2010).

Miller Pads and paper. Graph Paper Pad. No date specified. Http://millerpadsandpaper.com/graph-paper-pad/ (Year 0).

Shutterstock. Abstract black geometric background. Dots and line. By Djem. No date specified. https://www.shutterstock.com/image-vector/abstract-black-geometric-background-dots-line-232331239 (Year 0).

Target. Band-Aid Oh Joy! Adhesive Bandages—20 ct. No date specified. Https://www.target.com/p/band-aid-oh-joy-adhesive-bandages-20ct/-/A-17221637 (Year 0).

International search report dated Jun. 20, 2018, for international application PCT/US2018/027017.

International search report dated Jun. 20, 2018, for international application PCT/US2018/027018.

International search report dated Jun. 18, 2018, for international application PCT/US2018/027022.

International search report dated Jun. 18, 2018, for international application PCT/US2018/027024.

International Search Report—PCT/US2018/027019 dated Jun. 18, 2018.

Amazon, Band-Aid Brand Flexible Fabric Adhesive Bandages for Wound Care and First Aid, Finger and Knuckle, 20 ct (Pack of 6), Sep. 9, 2006, https://www.amazon.com/Band-Aid-Flexible-Adhesive-Bandages-Knuckle/dp/B000061DL7 (Year 2006).

Devine Express. Guardian Advantage Series Butterfly Electrodes Butterfly Tape Patch, Mini-Snap, 0.875" cs/50-32840. No date specified. https://bit.ly/314Bijc (Year: 0).

Amazon, Band-Aid Brand SKINFLEX Adhesive Banages for First Aid and Wound Care All One Size ct. 25 Count, Jan. 30, 2017, https://www.amazon.com/Band-Aid-Brand-Skin-Flex-Adhesive-Bandages/dp/B01M1K2MCO (Year: 2017).

Amazon, Band-Aid Brand Adhesive Bandage Family Variety Pack, Sheer and Clear Bandages, Assorted Sizes, 280 ct., Jun. 23, 2006, https://amzn.to/3vfLw3h (Year 2006).

* cited by examiner

EXTENSIBLE DRESSINGS

CROSS-REFERENCE TO RELATED APPLICATION

The present application claims the benefit of the earlier filing date of U.S. provisional patent application 62/483,989, filed Apr. 11, 2017, the entirety of which application is hereby incorporated by reference herein as if fully set forth herein.

FIELD OF THE INVENTION

The present invention relates to dressings such as bandages or tapes having improved extensibility and conformability to human skin and joints.

BACKGROUND OF THE INVENTION

Dressings such as bandages and tapes for applying to and/or covering the skin have been known for some time. Such dressings have gained wide acceptance for closing minor wounds, protecting minor wounds and/or covering abrasions. In some instances, microporous or breathable, bandages or tapes have been developed and are used either to cover minor wounds (including wounds that have been partially healed).

While such dressings have been greatly improved over the years in that, for example, they have incorporated microporous materials allowing the wound to breath and permitting water vapor to escape from the wound, hence, reducing chances of wound maceration, there remains a need for dressing which provide improved extensibility and elasticity of the dressing such that the dressing will cover and accommodate the dimensional contours of skin or tissues and move with (i.e., accommodating movement of) that portion of the skin or tissues covered by or in contact with the dressing, particularly in the situation where the dressing covers or is in contact with areas of the human tissue associated with jointed regions such as the joints of the fingers, ankles, elbows or knees. Accordingly, in order for a dressing to provide the aforementioned attributes, the dressing should also be able to dynamically conform to and with changing three dimensional contour of the skin or tissue surfaces to which it is applied.

The dressing should also be conformable to, or provide sufficient drapability, over the area human skin tissue contacted by the dressing or to which it is adhered.

It is, therefore, an aspect of the present invention to provide dressings that may be used to cover, protect wounds and facilitate wound healing. It is a further aspect of the present invention to provide bandages and tapes that conform to a wounded area of the skin and have improved extensibility, elasticity and conformability for better coverage of movable areas such as joints. Other aspects of the present invention will be readily apparent from the ensuing description and claims.

SUMMARY OF THE INVENTION

In one embodiment, the present invention relates to a dressing comprising a layer of material, the layer comprising a plurality of material free regions wherein the material free regions are in the form of sigmoid pattern units, the sigmoidal patterns having dimensions and oriented and arranged such that the layer of material extends in at least one of the 45° diagonal directions at least about 425% more than the same layer of material without material free regions, as measured by the Stretchability Test$_{xy}$ described in the Specification, when applying a force of from about 0.1 kgf along such 45° diagonal direction of the layer of material.

The present invention also relates to methods of using/applying the dressings of the present invention, including the disclosed embodiments, on skin surfaces covering jointed areas (or areas prone to movement) of human or mammalian bodies.

BRIEF DESCRIPTION OF THE DRAWINGS

An embodiment of this invention will now be described in greater detail, by way of illustration only, with reference to the accompanying drawings, in which.

DETAILED DESCRIPTION OF THE INVENTION

Figure 1:
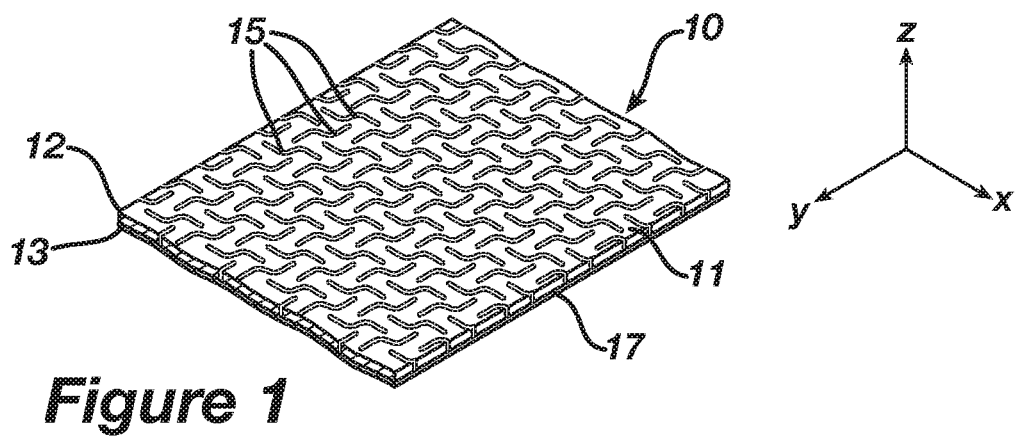
FIG. 1 is a perspective view of the dressing of the present invention with directional xyz-axis.

The dressing of the present invention can comprise, consist of, or consist essentially of the essential elements and limitations of the invention described herein, as well any of the additional or optional features, components, or limitations described herein.

The term "comprising" (and its grammatical variations) as used herein is used in the inclusive sense of (and, interchangeably with the terms) "having" or "including" and not in the exclusive sense of "consisting only of." The terms "a" and "the" as used herein are understood to encompass the plural as well as the singular.

As used herein, terms "skin" and "tissue" are interchangeable and refer to mammalian skin.

As used herein, the terms "visual inspection" or "visually inspected" means inspection with the unaided eye (excepting standard corrective lenses adapted to compensate for near-sightedness, farsightedness, or stigmatism, or other corrected vision) in lighting at least equal to the illumination of a standard 75 watt incandescent white light bulb at a distance of about 0.25 meter.

All documents incorporated herein by reference, by portion or in their entirety, are only incorporated herein to the extent that they are not inconsistent with this specification.

In certain embodiments, the present invention as disclosed herein may be practiced in the absence of any component, element (or group of components or elements) or method step which is not specifically disclosed herein.

Layer of Material

In certain embodiments, dressing 10 can be in the form of a wound dressing. In certain embodiments, dressing 10 can be in the form of a bandage or tape. Referring to the drawings, in FIG. 1, there is shown an exemplary embodiment of the improved dressing 10 of the present invention. In certain embodiments, the dressing 10 comprises a layer of material 11 formed from a woven or a nonwoven, non-swellable material. In one embodiment, the layer of material 11 is formed from a non-swellable, nonwoven material. The term "non-swellable" as used herein means materials that are incapable or substantially incapable of imbibing fluid such that there is little or no increase in the volume of the layer of material when it is in contact with fluid present in the environment of use, i.e., wound exudate or excretions or bodily sweat. In one embodiment, the layer of material increases in volume by no greater than about 5%, optionally, no greater than about 2.5%, optionally, or optionally, no greater than about 1% by weight aqueous saline solution based on the dry weight of the layer of material. These values may be obtained using a saline absorbency test in which a dry, weighed sample of layer of material is immersed for 1 minute at 37° C. in saline containing 0.9 wt. % NaCl for subsequent weighing.

Suitable non-swellable material includes, but is limited to, (or selected from or selected from the group consisting of) polyurethanes, polyethylene, polyisobutadiene, polyisobutylene, neoprene, polyamides, polyesters, polyether polyesters, non-hydrophilic polyether-polyamides, plasticised polyvinyl chloride, styrene-butadiene block copolymers, styrene-isoprene block copolymer, polyacrylates, methacrylic copolymers, polypropylene, rayon, rayon/polyester blends and mixtures thereof.

In certain embodiments, the non-swellable material is polyurethane. Suitable polyurethanes include, polyester and polyether polyurethanes examples of which are the Estanes (Registered trade mark of B.F. Goodrich Ltd). Suitable Estanes are those grades which are designated 5702, 5701, 5714F and 580201.

In certain embodiments, the non-swellable material is polyester. Suitable polyesters include polyethylene terephthalate (PET), polybutylene terephthalate (PBT) and mixtures thereof. PET substrates are commercially available from Fibertex Nonwovens (Ingleside, Ill.).

In certain embodiments, the layer of material is free of or substantially free of swellable materials such as cross-linked polyvinyl alcohol, cross-linked polyvinyl pyrrolidone, hydrophilic polyurethanes, hydrophilic hydroxyalkyl esters of poly(meth) acrylic aid and copolymers thereof, hydrophilic polyether-polyamide polymers, hydrophilic, water insoluble cellulosic derivatives such as cellulose acetate, cellulose acetate-proprionate. The term "substantially free of" as used herein means an amount of swellable materials of up to 5% (or about 5%), optionally, up to 2.5% (or about 2.5%), optionally, up to 1.0% (or about 1.0%), optionally up to 0.1% (or about 0.1%) by weight of the layer of material.

Figure 3:
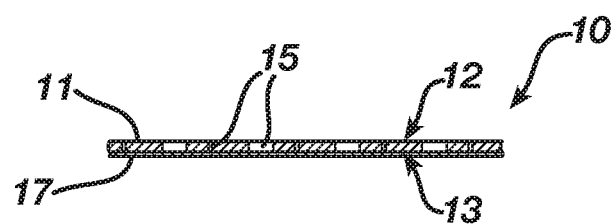
FIG. 3 is cross-sectional view of FIG. 2 taken along line 3-3.

In certain embodiments, the layer of material 11 is porous and readily allows both water vapor and air to pass through the layer of material 11. In certain embodiments, as may be seen in FIGS. 1 and 3, the top and bottom surfaces 12, 13 of the layer of material 11 are smooth and flat (or substantially smooth and flat) such that the top and bottom surfaces 12, 13 of the layer of material 11 are free of or substantially free of channels or raised portions in the surfaces.

In certain embodiments, the layer of material 11 may include channels or raised portions such as created by conventional embossing technology. In certain such embodiments, the channels or raised portions do not coincide with the pattern outlined by the sigmoidal pattern units discussed in further detail below. Examples of channels or raised portions can be found in US patent publications US20120220973 to Chan et al. and US20120220974 to Chan et al., each of which patent publications are herein incorporated by reference in its entirety.

In certain embodiments, the layer of material 11 has a thickness of from about 0.2 mm to about 3 mm, optionally from about 0.77 mm to about 1.5 mm.

Material Free Regions

The layer of material 11 of dressing 10 further incorporates one or more (or, plurality of) distinct material free regions 15 extending through the thickness (i.e., distance from top to bottom surfaces 12, 13) of the layer of material 11. The term "material free" or "free of material" as used herein means regions or areas of the layer of material that are free of material or substantially free of material such that the continuity of the material is disrupted or such regions or areas are devoid of material and include but not limited to, cuts, holes, slits or openings in the material. Accordingly, the terms "cuts", "holes", "slits" or "openings" in the material are interchangeable with each other and with the term "material free region". In certain embodiments, the distinct material free regions 15 include such distinct regions which may not be discernable by the naked eye (i.e., viewing without the aid of optical lenses which magnify the field of view); examples of such include ultra-thin slits formed in the layer of material 11 by cutting the layer of material 11 with a knife thickness of about 1 μm to about 25 μm, or a laser having laser thickness of about 10 μm to 1000 μm.

In certain embodiments, the distinct material free regions 15 are individual slits forming discrete, non-straight line, continuous, pattern units, each pattern unit being spaced from and unconnected to the other pattern units (for example, as in the discrete sigmoidal shaped pattern units shown in the Figures). In one embodiment, the slitted pattern units may be arranged in rows staggered from those on the next row or aligned with the slitted pattern units on the next row. In an alternative embodiment, the slitted pattern units of one row may be at right angles to the slitted pattern units of any adjacent row. In certain embodiments, the distinct material free regions 15 are sigmoidal shaped slits.

In certain embodiments, the pattern units (or slitted pattern units) 15 are formed into the layer of material 11 and have dimensions so as to provide a pattern surface density (i.e., pattern units 15 spatially arranged per square inch of the surface of the layer of material 11) of from 4 pattern units/in$^2$ to 14 pattern units/in$^2$, optionally from 10 pattern units/in$^2$ to 14 pattern units/in$^2$, or, optionally 12 pattern units/in$^2$ of the surface of the layer of material 11 when counting full and complete pattern units (i.e., partial or incomplete patterns are not counted when determining the pattern surface density). Varying (or scaling) the pattern surface density outside (i.e., either below or above) the described 4 pattern units/in² to 14 pattern units/in² range reduces any increase in extensibility of layer of material 11 provided by the incorporated pattern units (or material free regions) 15.

Figure 2:
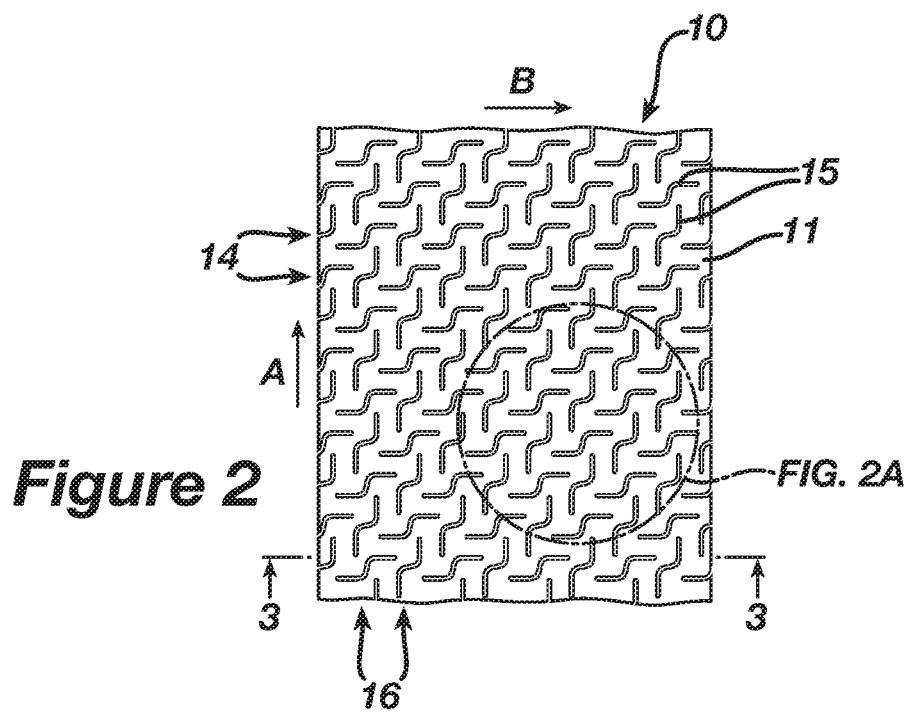
FIG. 2 is a plan view of the figure of FIG. 1.

One embodiment of the distinct material free regions 15 is illustrated in FIG. 2 showing the distinct material free regions 15 formed as individual sigmoidal slit pattern units 15. The term "sigmoidal" as used herein means patterns generally shaped in the form of an "S" and includes curvilinear patterns such as having curves defined by the mathematical formula $S(t)=1/1+e^{-t}$ and non-curvilinear patterns such as "block" or angled-cornered "S" shapes as illustrated by the pattern units in the rows of FIG. 5A. In certain embodiments, one or more (or all) of the sigmoidal pattern units in FIG. 2 are replaced with the non-curvilinear pattern units of FIG. 5A, yet retaining the same arrangement of the pattern units as shown in FIG. 2).

In addition to lasers and knifes, the material free regions may also be incorporated into the layer of material 11 during the formation of the layer of material 11 such as by water jet cutting, high pressure steam cutting, ultrasound cutting or punch cutting and the like.

Figure 2A:
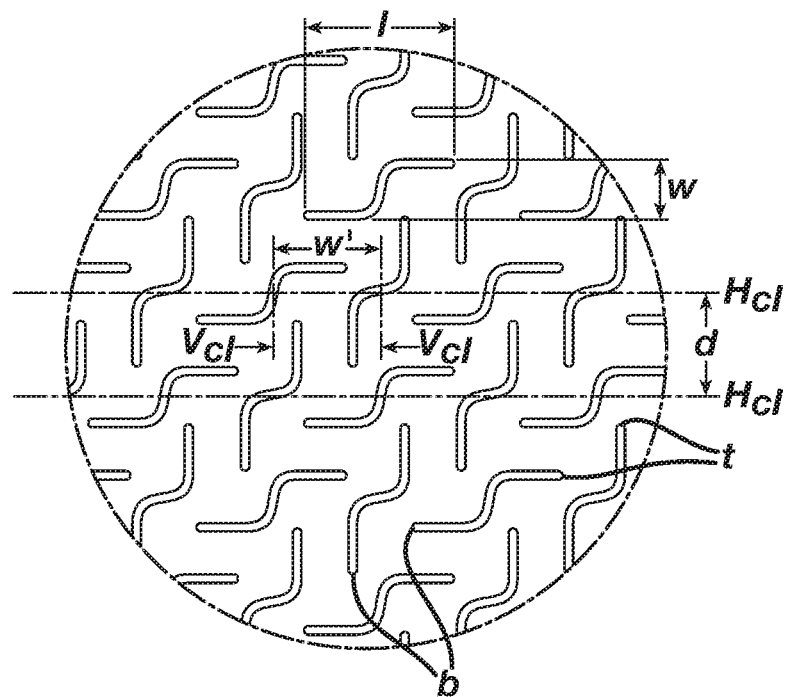
FIG. 2A is an enlarged top view of certain of the rows of pattern units of FIG. 2.

In certain embodiments, the sigmoidal slit pattern units 15 are arranged adjacent to one another. In certain embodiments, the sigmoidal slit pattern units 15 are non-intersecting and spaced apart relative to one another. Optionally, the sigmoidal slit pattern units 15 are further arranged to form one or more linear rows 14 of sigmoidal slit pattern units 15. In certain embodiments, the sigmoidal slit pattern units 15 are further arranged to form one or more linear rows 14 of sigmoidal slit pattern units 15 such that the top t and bottom b of any sigmoidal slit pattern unit 15 in a row 14 are spatially aligned with the respective top t and bottom b of the other similarly oriented sigmoidal slit pattern units 15 in that row (e.g., the top t and bottom b of any sigmoidal slit pattern unit 15 in a row 14 whose length l extends in one direction is spatially aligned with the top t and bottom b of any other sigmoidal slit pattern units 15 in that row whose length l extends in the same direction) as illustrated in FIG. 2A. The term "linear" as used herein means following straight, or substantially straight, line direction.

Figure 4A:
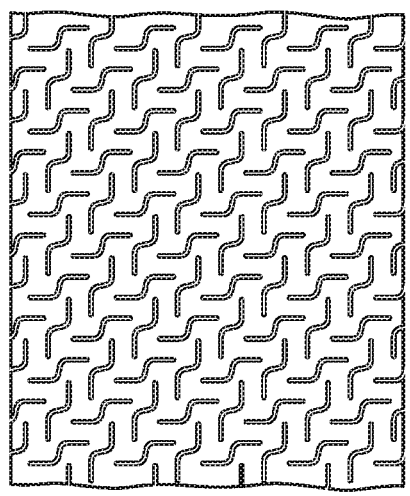
FIG. 4A shows the distinct material free regions in the closed position prior to application of force F.
Figure 4B:
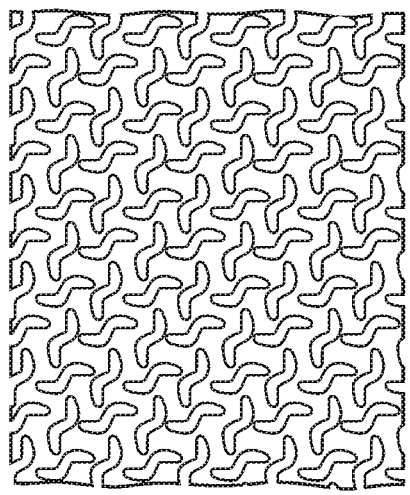
FIG. 4B shows the distinct material free regions in the open position during application of force F.
Figure 4C:
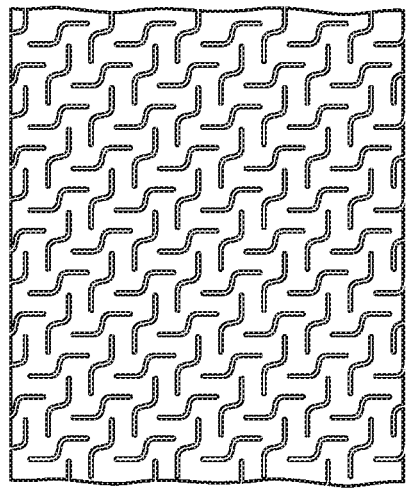
FIG. 4C shows the distinct material free regions returned to closed position after terminating application of force F.

In any of the above-described embodiments, when applied to the skin so as to cover or contact a wound and/or skin surface, the dressing 10 extends or stretches upon movement of the skin surface at or around such covered or contacted area so as to minimize detachment (i.e., loss of adherence to skin or wound) of dressing 10 as result of such movement. In such embodiments, any movement of the covered or contacted skin surface causes a force F (i.e., F>0) to the dressing 10. The sigmoidal slit pattern units 15 are arranged such that, after application of a force F (i.e., F>0) (in any direction) to the dressing 10, one or more of the material free regions freely open from a an initial closed position (or configuration) to an open position to facilitate stretching of the layer of material 11 from a first position p1 to second, stretched or extended, position p2 which is stretched or extended in the direction of the force F and wherein once the force F is no longer applied (i.e., F=0), the material free regions freely close (or return) to the initial closed position (or configuration) to facilitate movement of the layer of material 11 back to the first position p1 from the second position p2 as shown in FIGS. 4a, 4b and 4c. Accordingly, when an applied force is lessened or increased, the degree to which the one or more material free regions are opened is respectively decreased or increased. It is further understood that the material free regions 15 open in accordance with the direction of the force F. The term "freely" as used herein means that the material used to form the layer of material 11 will not swell so as to restrict or inhibit the opening or closing of the material free regions 15 and/or, once the releasable layer is removed, the layer of material 11 is not attached to any additional layer or substrate so as restrict or inhibit the opening or closing of the material free regions 15. The term "closed", "closed position" or "closed configuration", as used herein with respect to the material free regions 15, means that the material free regions 15 are closed or substantially closed such that there is no, or substantially no, visibility through the material free regions 15 upon visual inspection. The term "open", "open position" or "open configuration", as used herein with respect to the material free regions 15, means that the material free regions 15 are open such that there is visibility through the material free regions 15 upon visual inspection. The term "visibility" as used herein means the ability to see and identify distinct features of animate or inanimate objects.

As is shown in FIG. 2a, in certain embodiments, the length l of each sigmoidal slit pattern unit 15 can be large relative to its width w. In certain embodiments, the length l of the sigmoidal slit pattern unit 15 is from about 1 to about 6 times the width w of sigmoidal slit pattern unit 15, optionally the from 2.5 to about 4.7 times the width w. In certain embodiments, the length l of the sigmoidal slit pattern unit 15 is three times the width w of sigmoidal slit pattern unit 15.

Figure 8:
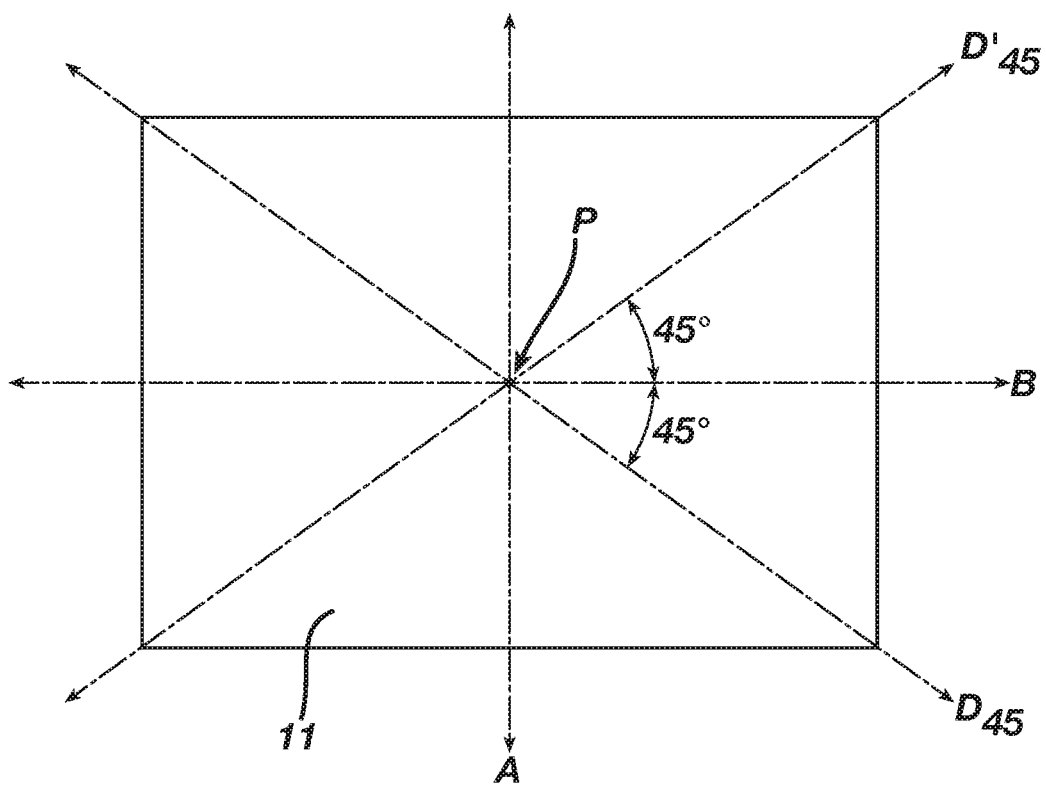
FIG. 8 shows the longitudinal, transverse and 45° diagonal directions (L, T and D$_{45}$) of the stretch force for the layer of material.

In certain embodiments, the length l of the sigmoidal slit pattern units 15 can be oriented to run in the transverse direction A of dressing 10 or to run in the longitudinal direction B of dressing 10. Transverse direction A is perpendicular to longitudinal direction B. Alternatively, one of more of the sigmoidal slit pattern units 15 can be arranged and oriented such that their lengths l run in the longitudinal direction B of dressing 10 and one or more of the sigmoidal slit pattern units 15 arranged or oriented such that one of more of the sigmoidal slit pattern units 15 run in the transverse direction A of dressing 10. Moreover, one of more of the sigmoidal slit pattern units 15 can be arranged and oriented such that their lengths l run in a direction diagonal to the transverse and longitudinal directions A and B. The term "diagonal" as used herein refers to a direction (or directional line) which forms an angle other than a right angle upon intersecting either the transverse or longitudinal directions A and B. Diagonal direction $D_{45}$ of FIG. 8 is an example of a direction diagonal to the transverse and longitudinal directions A and B.

In other embodiments, the length l sigmoidal slit pattern units 15 are oriented such that the length l of a sigmoidal slit pattern unit 15 is directionally perpendicular to the length l of an adjacent sigmoidal slit pattern unit 15. In one embodiment, as shown in FIGS. 1, 2 and 2A, the length l of the sigmoidal slit pattern units 15 are oriented such that the length l of each sigmoidal slit pattern unit 15 in a row 14 is oriented directionally perpendicular to its adjacent sigmoidal slit pattern unit 15 in such row 14.

Figure 5A:
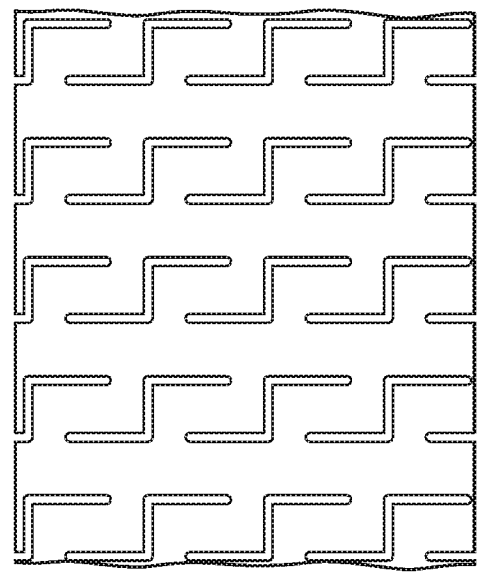
FIG. 5A shows a differently formed (or non-curvilinear) sigmoidal pattern units suitable for use in dressing of the present invention arranged where the pattern units in a row are aligned with respect to the pattern units in its adjacent rows.
Figure 5B:
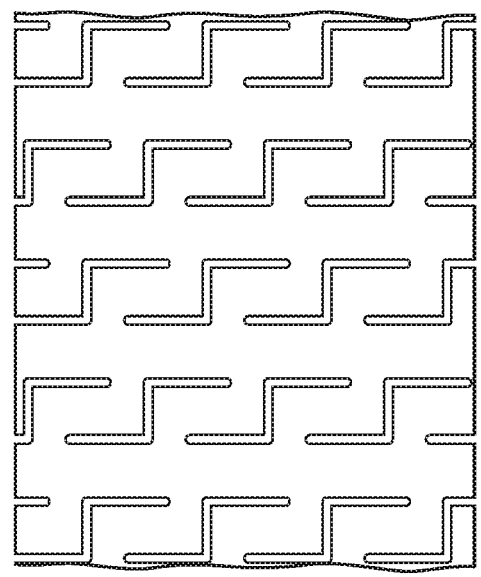
FIG. 5B shows the pattern of FIG. 5A where the pattern units in a row are off set with respect to the pattern units in adjacent rows.
Figure 5C:
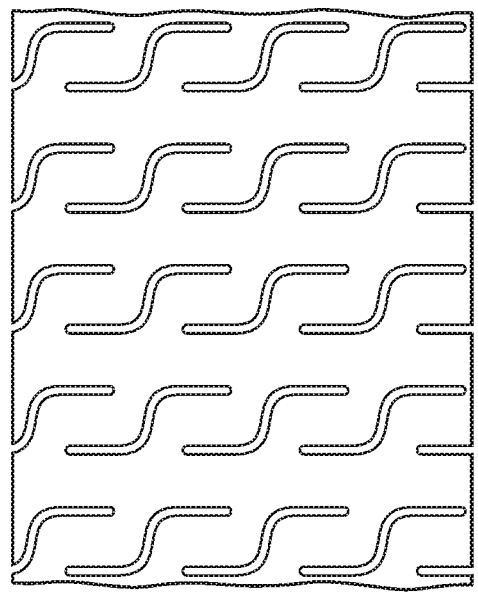
FIG. 5C shows sigmoidal pattern units of FIGS. 2 and 2A arranged where the pattern units in a row are aligned with respect to the pattern units in its adjacent rows.

In certain embodiments, the linear rows 14 of sigmoidal slit pattern units 15 are disposed adjacent to and parallel with other linear rows sigmoidal slit pattern unit 15. Where the linear rows of sigmoidal slit pattern units 15 are disposed parallel with other linear rows 14 of sigmoidal slit pattern unit 15, the stability of the layer of material upon application of a pulling force is reduced. As seen in FIGS. 5A and 5C, in certain embodiments, the linear rows 14 of sigmoidal slit pattern units 15 be arranged so that the sigmoidal slit pattern units 15 of one such row 14 are: i) aligned with respect to the sigmoidal slit pattern units 15 of an adjacent parallel row 14 (such that the aligned sigmoidal slit pattern units 15 of the rows 14 form an aligned column 16 of sigmoidal slit pattern units 15); or, alternately as shown in FIG. 5C, ii) staggered with respect to the sigmoidal slit pattern units 15 of an adjacent parallel row 14 (such that the sigmoidal slit pattern units 15 of one row 14 are offset from the sigmoidal slit pattern units 15 of any adjacent parallel row 14).

In certain embodiments, the length l ranges from 1 (or about 1) mm to 10 (or about 10) mm. In certain embodiments, the length l is from 4 (or about 4) mm to 8 (or about 8) mm. In certain embodiments, the width w ranges from 1 (or about 1) mm to 10 (or about 10) mm. In certain embodiments, the width w is from 3 (or about 3) mm to 4 (or about 4) mm.

The sigmoidal slit pattern unit 15 can be curvilinear or non-curvilinear. The term "curvilinear" as used herein means formed, bounded, or characterized by curved lines and free of angled edges or segments.

As further shown in FIG. 2a, in certain embodiments, each sigmoidal slit pattern unit 15 in a row 14 of sigmoidal slit pattern units 15 has a vertical centerline Vcl such that the vertical centerline Vcl of each sigmoidal slit pattern unit 15 is spaced from the vertical centerline Vcl of each other longitudinally, linearly adjacent sigmoidal slit pattern unit 15 by a width w'. And, in certain embodiments, each row 14 of sigmoidal slit pattern units 15 has a horizontal centerline Hcl. In certain embodiments, the horizontal centerline Hcl of each row 14 of sigmoidal slit pattern units 15 is spaced from the horizontal centerline Hcl of each other row 14 of sigmoidal slit pattern units 15 by a distance d. The vertical centerline Vcl is perpendicular to horizontal centerline Hcl.

The term "centerline" means a straight line intersecting and passing vertically or horizontally through the longitudinal center or transverse center, respectively, of either the distinct units of material free regions 15 or row 14 of distinct units of material free regions 15.

In certain embodiments, distance d is equal to width w'. In certain embodiments, the width w' ranges from 2.5 (or about 2.5) mm to 10 (or about 10) mm. In certain embodiments, the width w' is 6.5 (or about 6.5) mm. In certain embodiments, the distance d ranges from 2.5 (or about 2.5) mm to 10 (or about 10) mm. In certain embodiments, the distance d is 6.5 (or about 6.5) mm.

In certain embodiments, the plurality sigmoidal slit pattern units 15 and/or rows 14 are formed into the layer of material 11 at a surface density (i.e., slit pattern units/per in$^2$) to cover from about 50% to about 100%, optionally at least about 75% to about 100%, optionally from about 90% to about 100%, or optionally 100% (or about 100%), of the surface area of a surface (of both top and bottom planar surfaces) of the layer of material 11. As used herein, "cover 100% of the surface area of a surface of the layer of material" or "100% surface area coverage of the surface of the layer of material" or means that a plurality of slit pattern units are arranged at a surface density (i.e., slit pattern units/per in$^2$) and the plurality of slit pattern units cover the entire surface area of the surface of the layer of material and extend to the perimeter edges of the layer of material.

Without being limited by theory, it is believed the above-described sigmoidal slit pattern units 15 provide improved extensibility and conformability properties to dressing 10 by permitting stretch (or movement) in the longitudinal, transverse and diagonal (i.e., directionally neither longitudinal [or horizontal] nor transverse [or vertical] directions of the xy plane. In certain embodiments, the above-described sigmoidal slit pattern units 15 permit stretch (or movement) in the z axis direction. By utilizing this sigmoidal slit pattern, the dressing 10 unexpectedly requires less force in extending the dressing 10 as compared with the same dressing not incorporating the above-described sigmoidal slit pattern units 15.

Drapability

In certain embodiments, layer of material 11 comprising the material free slit pattern units of the present invention provides improved drapability. In certain embodiments, the material free slit pattern units of the present invention improves drapability of the layer of material without any slits by at least 30% based on the Bending Length of the layer of material tested for the longitudinal direction and by at least 50% in at least one of the two 45° diagonal directions based on the Bending Length of the layer of material tested in both two 45° diagonal directions as illustrated by longitudinal and 45° diagonal directions (B, $D_{45}$ and $D'_{45}$) in FIG. 8. The Bending Lengths and percent drapability are determined using the following Drapability Test.

Drapability Test (Stiffness Test)

The stiffness tester to be used in performing the Drapability Test consists of a platform, having a smooth low friction, flat plastic surface and calibrated scale. A rectangular strip of fabric is supported on a horizontal platform of the stiffness tester and extended in the direction of its length, so that an increasing part overhangs and bends under its own mass. The platform is supported by two side pieces made of plastic. Index lines are engraved on these side pieces, inclined at an angle of 41.5° below the plane of the platform surface. At this angle, the bending length is the overhanging length divided by two. A mirror is attached to the Stiffness Tester to enable the operator to view both index lines from a convenient position. A calibrated scale is supplied with the Stiffness Tester to measure the bending length and is graduated in cm. The test is conducted at 24.5° C. and 40% relative humidity.

Sample Preparation:

Test (i.e., with material free slit pattern units) and Control (i.e., without slits) samples are cut from a layer of material (described below) along the longitudinal and transverse directions and along the two 45° diagonal directions as illustrated by longitudinal, transverse and 45° diagonal directions (B, A, $D_{45}$ and $D'_{45}$) in FIG. 8 4. Three 8"×1" samples are cut for each of the longitudinal direction, transverse direction and along the two 45° diagonal directions for the Test samples. Three 8"×1" samples are cut for each of the longitudinal direction, transverse direction and along the two 45° diagonal directions for the Control samples. The samples are conditioned for 24 hours at a relative humidity of 50% and a temperature 23° C.

i. The layer of material used in preparing the samples is a bilayer substrate comprised of:

A nonwoven layer manufactured from 100% PET fibers having a fiber length about 38 mm by passing the fibers through a dry-laid carding process to form a blanket roll and then passed through a needle punching process. The nonwoven has a weight of 3.7 oz/square yard.

A layer of nonstick, HDPE net is heat laminated onto the nonwoven substrate. The net has the following properties:

Thickness=102-127 microns

Boss Count: longitudinal direction: 22-28 bosses/inch/transverse 27-33 bosses/inch Aperture (hole) size about 300 μm Basis weight=0.48-0.59 oz/sq yd Geometry=hexagonal Such HDPE nets are available from Delnet Technologies (Del.) under Delnet® AC530WHT net.

The above described bilayer material can be obtained from Delstar Technologies, DEL under the name Stratex™ 3.7NPET-E (which incorporates the Delnet® AC530WHT net).

Procedure:
a) The Stiffness Tester is placed on a level surface and the levels are checked with the help of the sprit level.
b) One of the conditioned Test samples cut out of one of the directions of the layer of material is placed flat on the flat plastic surface of the Tester in the length direction with leading edge of sample coincident with edge of flat plastic surface at point of incline.
c) The calibrated scale is gently put on the Test sample at the zero calibrated position.
d) The index lines the side pieces of the Stiffness Tester is viewed in the mirror of the Stiffness Tester.
e) The calibrated scale is then gently slid till the leading edge of the Test sample bends downward away from the calibrated scale and touches the two inclined index lines as viewed in the mirror.
f) In case the leading edge of the Test Sample is twisted, make the center point of the leading edge coincide with the plane. If the twist is more than 45°, disregard the reading.
g) The reading on the calibrated scale is recorded.
h) Steps b) through g) are repeated again with the opposite surface of Test sample positioned upwards and, then, two more times in the width direction—one for each surface of Test sample in the width direction.
i) The average of the 4 measured bending lengths are determined and recorded for the Test sample.
j) Steps b) through i) are repeated for each of the remaining Test samples cut out of same the direction of the layer of material.
k) The average of the bending lengths for each of the 3 Test samples in the same direction are averaged and recorded as the sample mean (referred to herein as the "Bending Length") for the samples in the same direction.
l) Steps b) through k) are repeated for the Test samples cut from the remaining directions.
m) Steps b) through l) are repeated in the same way by using the conditioned Control samples instead of Test samples.
n) The percent drapability of the slit containing layer of material along a given direction is calculated by dividing the Bending Length of the Test Sample cut out in that given direction by the Bending Length of the Control Sample cut out in that given direction.

Extensibility Along at Least One of the Longitudinal and Transverse Directions

In certain embodiments, the layer or material 11 with the sigmoidal slit pattern units 15 stretches or extends in at least one of the longitudinal B or transverse A directions at least 100% (or about 100%), optionally at least 150% (or about 150%), optionally at least 200% (or about 200%), optionally at least 300% (or about 300%), optionally at least 400% (or about 400%), or optionally at least 450% (or about 450%), or optionally at least 475% (or about 475%) more than the same layer of material 11 without material free regions, as measured by the Stretchability Test$_{xy}$ described in the Specification when a force of 0.1 (or about 0.1) kgf along is applied along such at least one of the longitudinal B or transverse A directions of the layer of material 11.

In certain embodiments, the layer or material 11 with the sigmoidal slit pattern units 15 stretches or extends in at least one of the longitudinal B or transverse A directions at least 150% (or about 150%), at least 200% (or about 200%), at least 250% (or about 250%), optionally at least 300 (or about 300%), optionally at least 350% (or about 350%), optionally at least 400% (or about 400%), optionally at least 500 (or about 500%), optionally at least 600% (or about 600%), optionally at least 700% (or about 700%), optionally at least 800% (or about 800%), optionally at least 825% (or about 825%), optionally at least 850% (or about 850%), or optionally at least 870% (or about 870%), more than the same layer of material 11 without material free regions, as measured by the Stretchability Test described in the Specification when a force of 0.2 (or about 0.2) kgf is applied along such at least one of the longitudinal B or transverse A directions of the layer of material 11.

In certain embodiments, the layer or material 11 with the sigmoidal slit pattern units 15 stretches or extends in at least one of the longitudinal B or transverse A directions at least 425% (or about 425%), optionally at least 450 (or about 450%), optionally at least 500% (or about 500%), optionally at least 550% (or about 550%), optionally at least 600% (or about 600%), optionally at least 650% (or about 650%), optionally at least 700% (or about 700%), optionally at least 750% (or about 750%), optionally at least 800% (or about 800%), optionally at least 900% (or about 900%), optionally at least 1000% (or about 1000%), optionally at least 1025% (or about 1025%), or optionally at least 1050% (or about 1050%), more than the same layer of material 11 without material free regions, as measured by the Stretchability Test described in the Specification when a force of 0.3 (or about 0.3) kgf is applied along such at least one of the longitudinal B or transverse A directions of the layer of material 11.

In certain embodiments, the layer or material 11 with the sigmoidal slit pattern units 15 stretches or extends in at least one of the longitudinal B or transverse A directions at least 650% (or about 650%), optionally at least 700% (or about 700%), optionally at least 750% (or about 750%), optionally at least 800% (or about 800%), optionally at least 900% (or about 900%), optionally at least 1000% (or about 1000%), optionally at least 1050% (or about 1050%), optionally at least 1100% (or about 1100%), optionally at least 1125% (or about 1125%), or optionally at least 1150% (or about 1150%), more than the same layer of material 11 without material free regions, as measured by the Stretchability Test described in the Specification when a force of 0.4 (or about 0.4) kgf is applied along such at least one of the longitudinal B or transverse A directions of the layer of material 11.

Extensibility Along the Other (or Remaining) Longitudinal and Transverse Directions In certain embodiments, where stretching or extensibility of at least one of the longitudinal or transverse directions is determined as above using the Stretchability Test$_{xy}$ described in the Specification, the other (or remaining) longitudinal or transverse direction can likewise be determined using the Stretchability Test$_{xy}$ described in the Specification. In the case of such "other" longitudinal or transverse direction:
in certain embodiments, the layer or material 11 with the sigmoidal slit pattern units 15 stretches or extends in the other longitudinal B or transverse A direction at least 75% (or about 75%), optionally at least 100% (or about 100%), optionally at least 125% (or about 125%), optionally at least 150% (or about 150%), optionally at least 175% (or about 175%), or optionally at least 190% (or about 190%), more than the same layer of material 11 without material free regions, as measured by the Stretchability Test$_{xy}$ described in the Specification, when a force of from 0.1 (or about 0.1) kgf is applied along such other longitudinal B or transverse A direction of the layer of material 11.

in certain embodiments, the layer or material 11 with the sigmoidal slit pattern units 15 stretches or extends in the other longitudinal B or transverse A direction at least 150% (or about 150%), optionally at least 200% (or about 200%), optionally at least 250% (or about 250%), optionally at least 300% (or about 300%), optionally at least 350% (or about 350%), optionally at least 375% (or about 375%), or optionally at least 390% (or about 390%), more than the same layer of material 11 without material free regions, as measured by the Stretchability Test$_{xy}$ described in the Specification when a force of from 0.2 (or about 0.2) kgf is applied along such other longitudinal B or transverse A direction of the layer of material 11.

in certain embodiments, the layer or material 11 with the sigmoidal slit pattern units 15 stretches or extends in the other longitudinal B or transverse A direction at least 350% (or about 350%), optionally at least 400% (or about 400%), optionally at least 425% (or about 425%), optionally at least 450% (or about 450%) or optionally at least 475% (or about 475%)_more than the same layer of material 11 without material free regions, as measured by the Stretchability Test$_{xy}$ described in the Specification when a force of from 0.3 (or about 0.3) kgf is applied along such other longitudinal B or transverse A direction of the layer of material 11.

Diagonal Extension

In certain embodiments, the layer or material 11 with the sigmoidal slit pattern units 15 stretches or extends in at least one of the 45° diagonal direction $D_{45}$ or $D'_{45}$ at least 425% (or about 425%), optionally at least 450% (or about 450%), optionally at least 500% (or about 500%), optionally at least 550% (or about 550%), optionally at least 600% (or about 600%), optionally at least 700% (or about 700%), optionally at least 800% (or about 800%), optionally at least 900% (or about 900%), optionally at least 1000% (or about 1000%), optionally at least 1100% (or about 1100%), optionally at least 1200% (or about 1200%), or optionally at least 1300% (or about 1300%), optionally at least 1400% (or about 1400%), optionally at least 1500% (or about 1500%), optionally at least 1600% (or about 1600%), optionally at least 1700% (or about 1700%), or optionally at least 1800% (or about 1800%), optionally at least 1900% (or about 1900%), optionally at least 2000% (or about 2000%), optionally at least 2100% (or about 2100%), optionally at least 2200% (or about 2200%), or optionally at least 2300% (or about 2300%), optionally at least 2350% (or about 2350%) or optionally at least 2375% (or about 2375%), more than the same layer of material without the sigmoidal slit pattern units 15, as measured by the Stretchability Test$_{xy}$ described in the Specification when a force of 0.1 (or about 0.1) kgf is applied along such 45° diagonal direction $D_{45}$ or $D'_{45}$ of the layer of material 11. The "45° diagonal direction $D_{45}$" or "45° diagonal direction $D'_{45}$" refers to diagonally directional lines of force extending through center point P and forming a 45° angle with the longitudinal and traverse centerlines of the layer of material 11 intersecting at center point P.

In certain embodiments, the layer or material 11 with the sigmoidal slit pattern units 15 stretches or extends in at least one of the 45° diagonal direction $D_{45}$ or $D'_{45}$ at least 1125% (or about 1125%), optionally at least 1150% (or about 1150%), optionally at least 1175% (or about 1175%), optionally at least 1200% (or about 1200%), or optionally at least 1300% (or about 1300%), optionally at least 1400% (or about 1400%), optionally at least 1500% (or about 1500%), optionally at least 1600% (or about 1600%), optionally at least 1700% (or about 1700%), optionally at least 1800% (or about 1800%), optionally at least 1900% (or about 1900%), optionally at least 2000% (or about 2000%), optionally at least 2100% (or about 2100%), optionally at least 2200% (or about 2200%), optionally at least 2300% (or about 2300%), optionally at least 2400% (or about 2400%), optionally at least 2500% (or about 2500%), or optionally at least 2550% (or about 2550%), more than the same layer of material without the sigmoidal slit pattern units 15, as measured by the Stretchability Test$_{xy}$ described in the Specification when a force of 0.2 (or about 0.2) kgf is applied along such 45° diagonal direction $D_{45}$ or $D'_{45}$ of the layer of material 11.

In certain embodiments, the layer or material 11 with the sigmoidal slit pattern units 15 stretches or extends in at least one of the 45° diagonal direction $D_{45}$ or $D'_{45}$ at least 1725% (or about 1725%), optionally at least 1800% (or about 1800%), optionally at least 1800% (or about 1800%), optionally at least 1900% (or about 1900%), optionally at least 2000% (or about 2000%), optionally at least 2100% (or about 2100%), optionally at least 2200% (or about 2200%), optionally at least 2300% (or about 2300%), optionally at least 2325% (or about 2325%), or optionally at least 2350% (or about 2350%), more than the same layer of material without the sigmoidal slit pattern units 15, as measured by the Stretchability Test$_{xy}$ described in the Specification when a force of 0.3 (or about 0.3) kgf is applied along such 45° diagonal direction $D_{45}$ or $D'_{45}$ of the layer of material 11.

In certain embodiments, the layer or material 11 with the sigmoidal slit pattern units 15 stretches or extends in at least one of the 45° diagonal direction $D_{45}$ or $D'_{45}$ at least 1650% (or about 1650%), optionally at least 1700% (or about 1700%), optionally at least 1750% (or about 1750%), optionally at least 1800% (or about 1800%), optionally at least 1800% (or about 1800%), optionally at least 1900% (or about 1900%), optionally at least 2000% (or about 2000%), optionally at least 2100% (or about 2100%), optionally at least 2125% (or about 2125%), or optionally at least 2150% (or about 2150%), more than the same layer of material without the sigmoidal slit pattern units 15, as measured by the Stretchability Test$_{xy}$ described in the Specification when a force of 0.4 (or about 0.4) kgf is applied along such 45° diagonal direction $D_{45}$ or $D'_{45}$ of the layer of material 11.

The above referenced longitudinal, transverse and 45° diagonal directions (B, A, $D_{45}$ and $D'_{45}$) of stretch or extension force used in conducting the Stretchability Test$_{xy}$ are in the xy-plane and are illustrated in FIG. 8. The term "longitudinal" direction refers to the machine direction of the layer of material when formed using a continuous manufacturing process. As used herein, the term "machine direction" means the direction along the length of the roll layer of material or the direction in which the material flows into the substrate forming machine in the continuous manufacturing process. The "transverse" direction is the direction transverse to the longitudinal direction.

In certain embodiments, the layer or material 11 with the sigmoidal slit pattern units 15, when applying a force of about 0.1 kgf along the z-axis of (or in the direction perpendicular to xy-plane of) the layer of material 11, stretches or extends along the z-axis or in the z direction about 1 mm to about 5 mm, optionally between about 4 mm to about 5 mm, away from the xy-plane of the layer of material 11, as measured by the Stretchability Test$_z$ described in the Specification.

In certain embodiments, the layer or material 11 with the sigmoidal slit pattern units 15, when applying a force of about 0.5 kgf along the z-axis of (or in the direction perpendicular to xy-plane of) the layer of material 11, stretches or extends along the z-axis or in the z direction about 1 mm to about 10 mm, optionally from about 1 mm to about 8 mm, or optionally between about 8 mm and 10 mm, away from the xy-plane of the layer of material 11, as measured by the Stretchability Test$_z$ described in the Specification.

In certain embodiment, to improve the stretchability or extensibility in the (or along the) z-axis (or the direction perpendicular to xy-plane) of the layer of material 11, the pattern units (or slitted pattern units) 15 are formed into the layer of material 11 having dimensions so as to provide a pattern surface density of from 4 pattern units/in$^2$ to 14, optionally from 10 to 14 pattern units/in$^2$, or optionally 12 pattern units/in$^2$.

In certain embodiments, the layer of material 11 with the sigmoidal slit pattern units 15 meets any one, any combination or all of the above described stretch parameters using the Stretchability Tests described below.

Stetchability Tests:

The directional extensibility of the dressings of the present invention are measured using procedures of the following the Stretchabilty Tests which include test procedures for testing stretching or extensibility of the layer of material along the longitudinal, transverse and 45° diagonal directions D$_{45}$ directions of the layer of material:

Stretchability Test$_{xy}$—Test to measure displacement of layer of material under force F along directions of in xy-plane of the layer of material.

The Stretchability Test$_{xy}$ is modeled after the ASTM D882, Standard Test Method for Tensile Properties of Thin Plastic Sheeting (ASTM International, West Conshohocken, Pa., 2016). The ASTM D882 procedure was slightly modified and performed as follows: a sample layer of material is clamped between two gripped flat surfaces, attached to a load cell in order to apply force tension at a constant-rate. The force is exerted against the sample extending both clamps in opposing directions (including opposing directions which are oriented longitudinally and transversely with respect to the sample and opposing directions which are oriented along the negatively and positively sloping 45° diagonal directions D$_{45}$ of the sample) until rupture occurs in the sample. Samples are measured in triplicate. The test is conducted at 23° C. and 50% relative humidity.

A. Apparatus:

The testing apparatus used is Instru-Met & Instron 1122 (Instru-Met Corporation, Union, N.J. 07083) with an Instru-Met Pneumatic Wedge Action Grips.

B. Procedure:
  a) Test samples (samples with material free slit pattern units) are prepared by cutting a layer material having the slits (or material free regions) of the present invention into 5 inches by 1 inch strips.
    i. The layer of material used in preparing the samples is a bilayer substrate comprised of:
      A nonwoven layer manufactured from 100% PET fibers having a fiber length about 38 mm by passing the fibers through a dry-laid carding process to form a blanket roll which is then passed through a needle punching process. The nonwoven has a weight of 3.7 oz/square yard.
      A layer of nonstick, HDPE net is heat laminated onto the nonwoven substrate. The net has the following properties:
        Thickness=102-127 microns
        Boss Count: longitudinal direction: 22-28 bosses/inch/transverse 27-33 bosses/inch
        Aperture (hole) size 300 μm
        Basis weight=0.48-0.59 oz/sq yd
        Geometry=hexagonal
      Such HDPE nets are available from Delnet Technologies (Del.) under Delnet® AC530WHT net.
      The above described bilayer material can be obtained from Delstar Technologies, DEL under the name Stratex™ 3.7NPET-E (which incorporates Delnet® AC530WHT net).
    ii. The slit pattern units formed into the layer of material are incorporated using a 90 watt CO$_2$ laser (Full Spectrum Laser [NV], Model P2012) having a laser thickness of 406 μm such that the slit pattern units are arranged as parallel rows of slit pattern units having the following the measurements:
      Slit pattern units provide a surface density of slit pattern units of 12 slit pattern units/in$^2$ (counting only complete pattern units)
      Slit pattern units cover 100% of surface area of surface of layer of material.
  b) Control samples (i.e. samples not having slits [or material free regions]) are prepared by cutting a layer material without the slits into 5 inch by 1 inch strips
    i. The layer of material used for this step is the same as the layer of material of step a).
  c) The test and control cut samples are conditioned by leaving them in a room which is 23±1° C. and 50±2% relative humidity for a period of twenty-four hours.
  d) The grips of testing apparatus are distanced 2" a part.
  e) A control sample to be tested is placed into the grips of testing apparatus, and fastened securely;
  f) There should be no tension in the sample.
  g) A force is applied to the sample in the machine direction (or longitudinal direction B) with the one grip remaining stationary and the other grip traveling in an opposing direction at a constant rate of speed as specified in the internal test standard (12 inches/min).
  h) Application of the force is continued until the sample yielded (i.e., there is a rupture anywhere in the sample).
  i) The applied force at percent displacements (or extensions) of length of the sample (along the respective directions of force) of 2%, 5%, 10%, 25% and 50% is recorded (as kgf) into an MTS Test Works 4.12 F software application (Instru-Met Corporation, NJ)
  j) A test sample is tested in accordance with steps e) through i).
  k) The above steps e) through j) are repeated two additional times using different test and control samples, respectively.
  l) The data recorded into the MTS Test Works 4.12 F software for the respective control and test samples at the 2%, 5%, 10%, 25% and 50% increments are then averaged and recorded.
  m) The percent difference in the directional extensions in the longitudinal (or machine direction) between the test sample and the control sample at a given force and force direction is calculated from the data recorded in the MTS Test Works 4.12 F software.

n) Steps a) through n) are repeated for the transverse direction A (or cross-direction) and each of the opposing "45°" diagonal directions $D_{45}$ (as illustrated in FIG. 8).

Stretchability Test$_z$ Test to measure displacement of layer of material under force F along the z-axis (or direction) of the layer of material.

The Stretchability Test$_z$ is modeled after the ASTM D3787-16, Standard Test Method for Bursting Strength of Textiles (ASTM International, West Conshohocken, Pa., 2016). The ASTM D3787-16 procedure was slightly modified and performed as follows: a sample is clamped between two grooved, circular plates. A second piece, a ball attachment, is secured to the load cell in order to apply compression by means of the constant-rate-of-traverse testing machine. The force is exerted against the specimen by a polished, hardened, steel ball until rupture occurs in the non-woven portion of the material. Testing of materials was performed to show displacements under load at specific ranges. Both non-woven and non-woven with laminates were tested. The test is conducted at 23° C. and 50% relative humidity.

A. Apparatus:

The testing apparatus used is Instru-Met & Instron 1122 & 5543 (Instru-Met Corporation, Union, N.J. 07083) with an ASTM D3787 Burst Fixture, including 44.5 mm ID ring clamp and 25.4 mm spherical plunger. The throat of the Burst Fixture was modified by extending it from its original length of 2.5" to a length of 3.75" and the springs under the clamping screws are removed to ensure clamping forces.

B. Procedure:

a) Test samples (samples with material free slit pattern units) are prepared by cutting the layer material into 3¾ diameter circle shaped cutouts.
  i. The layer of material used in preparing the samples is a bilayer substrate comprised of:
    A nonwoven layer manufactured from 100% PET fibers having a fiber length about 38 mm by passing the fibers through a dry-laid carding process to form a blanket roll which is then passed through a needle punching process. The nonwoven has a weight of 3.7 oz/square yard.
    A layer of nonstick, HDPE net is heat laminated onto the nonwoven substrate. The net has the following properties:
      Thickness=102-127 microns
      Boss Count: longitudinal direction: 22-28 bosses/inch/transverse
      27-33 bosses/inch
      Aperture (hole) size 300 μm
      Basis weight=0.48-0.59 oz/sq yd
      Geometry=hexagonal
    Such HDPE nets are available from Delnet Technologies (Del.) under Delnet® AC530WHT net.
    The above described bilayer material can be obtained from Delstar Technologies, DEL under the name Stratex™ 3.7NPET-E (which incorporates Delnet® AC530WHT net).
  ii. The slit pattern units formed into the layer of material are incorporated using a 90 watt $CO_2$ laser (Full Spectrum Laser [NV], Model P2012) having a laser thickness of 406 μm such that the slit pattern units are arranged as parallel rows of slit pattern units having the following the measurements:
    Slit pattern units provide a surface density of slit pattern units of 12 slit pattern units/in$^2$ (counting only complete pattern units)
    Slit pattern units cover 100% surface area of layer of material.

b) Control samples (i.e. samples not having slits [or material free regions]) were prepared by cutting a layer material without the slits into 5 inch by 1 inch strips
  i. The layer of material used for this step is the same as the layer of material of step a).

c) The test and control cut samples are conditioned by leaving them in a room which is 23±1° C. and 50±2% relative humidity for a period of twenty-four hours.

d) A sample to be tested is placed into the ring clamps of testing apparatus, and fastened securely;

e) There should be no tension in the sample.

f) A force is applied to the sample in the z direction (i.e., perpendicular to xy plane of the sample) with the spherical plunger at a constant rate of speed as specified in the internal test standard (25.4 mm/min) and then the speed was reduced to 5.08 mm/min.

g) Application of the force is continued until the sample yielded (i.e., there is a rupture anywhere in the sample).

h) The applied force at displacements (or extensions) of length of the sample (along the z-direction of force) of 1 mm, 2 mm, 3 mm, 4 mm, 5 mm, 6 mm, 8 mm, 10 mm, 15 mm, and 20 mm. was recorded (as kgf) into an MTS Test Works 4.12 F software application (Instru-Met Corporation, NJ)

i) A test sample is tested in accordance with steps d) through h).

j) The above steps d) through i) are repeated two additional times using different test and control samples, respectively.

k) The data recorded into the MTS Test Works 4.12 F software at the 1 mm, 2 mm, 3 mm, 4 mm, 5 mm, 6 mm, 8 mm, 10 mm, 15 mm, and 20 mm displacement increments are then averaged and recorded.

Moreover, the above-described sigmoidal slit pattern units 15 also provide dressing 10 which readily conform to or drape upon the tissue contacted or covered by dressing 10, permitting dressing 10 to move with the tissue, yet maintain skin and/or wound coverage or contact.

Releasable Layer

In certain embodiments, the dressing 10 (optionally, including any additional layers 20 [as discussed in more detail below]) also comprises a releasable layer 17 releasably disposed on (or in contact with): i) the layer of material 11; or ii) the dressing 10 comprising the layer of material 11. In certain embodiments, the releasable layer 17 releasably contacts and covers any adhesive that may be disposed on the layer of material 11. In some embodiments, the releasable layer 17 contacts (or, is releasably attached to) the layer of material 11 or the dressing 10 while (or when) the material free regions 15 are in the closed position. In some embodiments, the releasable layer 17 releasably contacts (or is releasably attached to) the layer of material 11 or the dressing 10 such that material free regions 15 are releasably retained in the closed position until such time as the releasable layer 17 is removed from the layer of material 11 or the dressing 10, thereby permitting the material free regions 15 to freely open upon the application of a force F as described above (and, correspondingly. close upon termination of such force F). In certain embodiments, the releasable layer 17 can comprise or be made of polyethylene, polypropylene, kraft papers, polyester or composites of any of these materials.

Optional Components

In certain embodiments, dressing 10 further incorporates on at least one of surfaces 12 and/or 13 an adhesive (not shown) and disposed between the releasable layer and the layer of material to provide adherence of the dressing 10 to the skin and/or wound. When incorporated onto dressing 10, the adhesive is applied so as not restrict or inhibit the freeness of the distinct material free regions freely opening and closing. In general, any of a variety of pressure-sensitive adhesives can be utilized as the adhesive. In particular, pressure-sensitive adhesives that are biocompatible with human skin are typically utilized. In some embodiments, an adhesive of the present invention may also be either generally water soluble or generally insoluble, or dispersible in an aqueous environment. For instance, commercially available dispersible pressure-sensitive adhesive is sold under the trade name of HL-9415-X and is available from H.B. Fuller Company. Another suitable adhesive includes about 10-75% by weight of a polyalkyloxazoline polymer, 10-75% by weight of a functional diluent comprising a hydroxy compound or a carboxylic acid compound, and 5-50% by weight of a tackifier.

The adhesive may comprise hydrocolloids. The hydrocolloid element used may be any substance that has a good performance in this utilization, as for example, sodium carboxymethylcellulose, pectin, xanthan gum, polysaccharides, sodium or calcium alginates, chitosan, seaweed extract (carrageenan), polyaspartic acid, polyglutamic acid, hyaluronic acid or salts and derivatives thereof, among others.

Hydrocolloids, just as sodium carboxymethylcellulose and pectin, among others, are agents that form gels as soon as they come into contact with the bodily fluids from the wound. When used in adhesive bandages, these hydrocolloids are combined with elastomers and/or adhesives. Preferably, the adhesive bandage should provide a humid environment but without saturation or cicatrisation, which is a situation suitable for acceleration of the healing, The adhesive may be any conventional adhesive known for such use, as for example pressure acrylic adhesives, among others. Additionally, such an adhesive may contain a resin for increasing adhesion, a cohesion increasing agent, an absorption agent (preferably a polyacrylate superabsorbent, a polyacrylate salt superabsorbent or a mixture thereof), a plasticizer and optionally a pigment. The adhesive may further be configured in discontinuous patterns, arranged in lines, screen, spray or any other which a person skilled in the art understands as discontinuous, composed by an elastomeric base.

Figure 6:
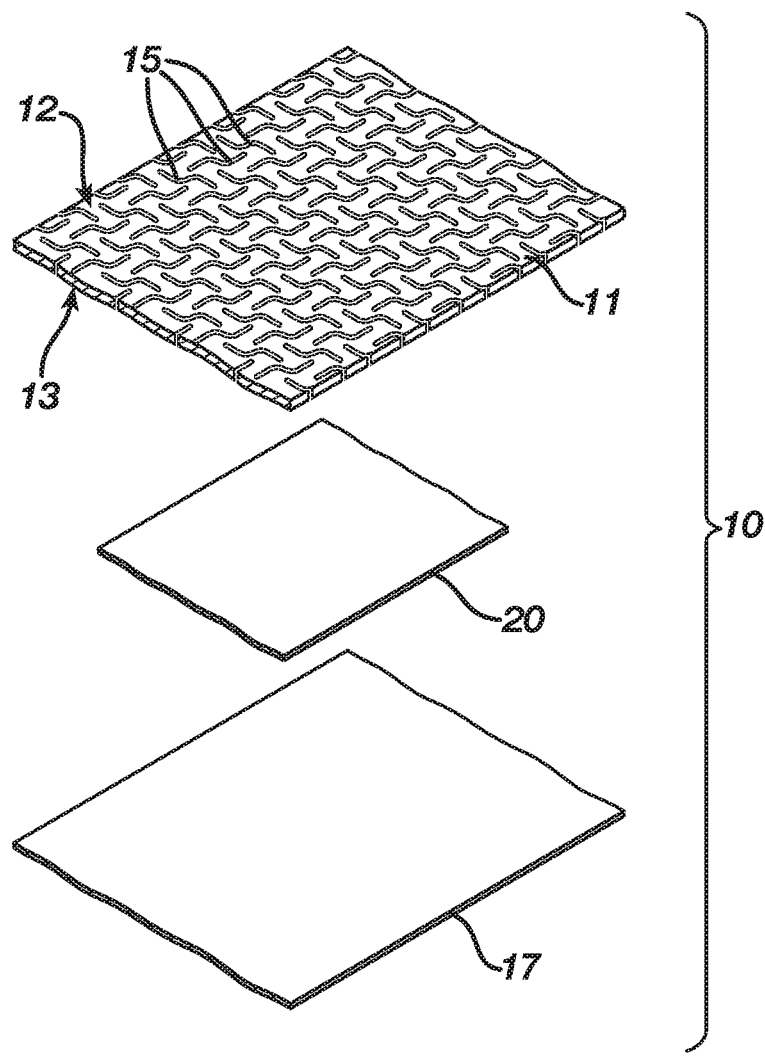
FIG. 6 is an exploded view of dressing of present invention showing an additional layer in between the layer of material of the present invention and the releasable layer.
Figure 7:
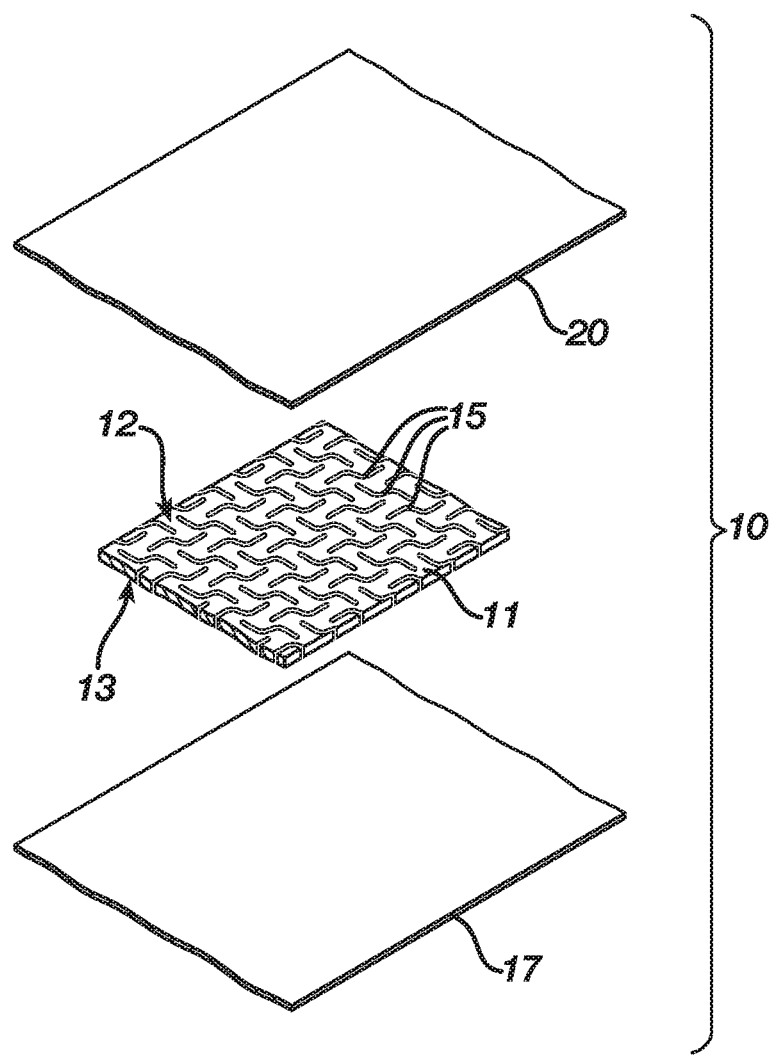
FIG. 7 is an exploded view of dressing of present invention showing the layer of material of the present invention in between a backing layer and the releasable layer.

Optionally, one or more additional layer(s) (or substrate layer(s)) 20 comprising a single or multiple layers (or substrate layers) is disposed on the layer of material 11, either on the surface side of the layer of material 11 which is opposite the releasable layer 17 or disposed between the layer of material 11 and releasable layer 17. In such embodiments, the layer of material 11 is not attached to any additional layer 20 such that additional layer 20 would significantly restrict or inhibit the opening or closing of the material free regions 15. In certain embodiments, the additional layer 20 may or may not incorporate the material free regions 15. In embodiments where the additional layer 20 incorporates the material free regions 15, the material free regions 15 in the additional layer 20 form the same or similar pattern units as the pattern units formed by the material free regions 15 in the layer of material 11; in certain of such embodiments, the pattern units of the additional layer 20 are also aligned with the pattern units of the layer of material 11. The additional layer 20, in the form of a single or multiple layer, may be incorporated to act as a protective backing layer for layer of material 11 as shown in FIG. 7. Or, such additional layer 20 may act as, or include, a pad layer, as shown in FIG. 6, providing absorbent and/or swelling properties. In certain embodiments, the additional layer 20 comprises the material free regions 15 (optionally, in the form of slitted patterns) of the present invention. In certain embodiments, the additional layer 20 is free of or substantially free of the material free regions of the present invention; in one such embodiment the additional layer 20 acts as a protective non-stick layer (with or without apertures) disposed on the surface of the layer of material 11 facing the skin of a user (and/or wound on such skin).

In certain embodiments, when additional layer 20 acts as a pad layer, additional layer 20 includes a first surface facing a first side of the layer of material 11, and that has a first surface area, and a second surface opposite the first surface and facing the skin, and that has a second surface area. The pad layer can be formed from open work, porous, natural or synthetic fibrous material, such as material used to form gauze. Suitable pad layer material include, but are not limited to, fibrous PET. The pad layer typically contacts the skin surface and/or wound to absorb wound exudate or excretions. In certain embodiments, when the additional layer 20 acts as a pad layer, the additional layer 20 can be affixed either directly or indirectly layer of material 11 so that it will not become separated from layer of material 11 during normal use.

When used as a backing layer, additional layer 20 may have various shapes, including but not limited to, rectangular, oval, ovoid, or oblong. In such an embodiment, the shape of the bandage and tape 10 defined by the shape of additional layer 20. In some such embodiments, additional layer 20 may be thin, highly flexible or deformable, water-impervious, and clear or opaque. General, in some such embodiments, the thickness of additional layer 20 is between about 0.05 to 0.2 millimeter ("mm") to achieve the forming and flexing characteristics desired.

In certain such embodiments, where additional layer 20 acts as a backing layer, the material used in forming the additional layer 20 should be both conformable to the contours of the body and flexible so as to permit free movement of the body part wearing the product. In certain embodiments, it can be a a film or a foam. Polymeric materials useful in forming backing layers include polyolefin (such as polyethylene), polyurethane, and polyvinylchloride. Other examples of backings include, but are not limited to, nonwoven, woven, or knitted fabrics such as cotton, polyester, polyurethane, rayon and the like.

Polyethylene film may be optional used to form additional layer 20 where additional layer 20 acts as a backing layer 20, and, in such instances, particularly effective results can be achieved with stretchable, elastomeric films formed of polyurethane, which has the further advantage of gas (including water vapor) transmissibility. It is to be understood, however, that, in such instances, other flexible, water insoluble polymeric films known in the art may be used. Furthermore, where additional layer 20 is used as a backing layer, additional layer 20 may be formed from closed-cell polymeric foam, particularly one with an integral skin covering the side of the closed-cell polymeric foam facing away from the skin of the user. In certain such embodiments, foam layers formed of polyurethane or polyethylenes are suitable, while other polymeric foams having similar properties may be used. In other embodiments, where additional layer 20 is used as a backing layer, additional layer 20 may be made from other polyolefins, vinyl polyethylene acetate, textile non-woven fabrics, rubber, or other materials known in the adhesive article art. In certain embodiments, polymers used to form additional layer 20 where additional layer 20 acts as a backing layer generally have viscosity of from about 500 to 500,000 centipoises at temperatures of about 190° C., or from about 1,000 to 30,000 centipoises at temperatures of about 190° C., or from about 3,000 to 15,000 centipoises at temperatures of about 190° C.

In certain embodiments, where additional layer 20 acts as a backing layer, additional layer 20 may be impermeable to liquid, but permeable to gas, which allows the wound and the skin to which the bandage and tape 10 of the present invention is adhered to breathe. In one embodiment, where additional layer 20 acts as a backing layer, additional layer 20 may have pores of such a size that will allow only the passage of gases, which have molecules of extremely small size.

Finally, where additional layer 20 acts as a backing layer, additional layer 20 may be perforated for still further ventilation of the skin. In certain such embodiments, perforations may be circular in area and have a range of diameters, such as from about 0.1 to about 0.8 millimeters. In certain other embodiments, however, where additional layer 20 acts as a backing layer, additional layer 20 may, when necessary, be totally impermeable to gases.

The present invention is further described by the following example which is presented for purposes of illustration and comparison:

EXAMPLES

Comparative Example 1

Figure 9:
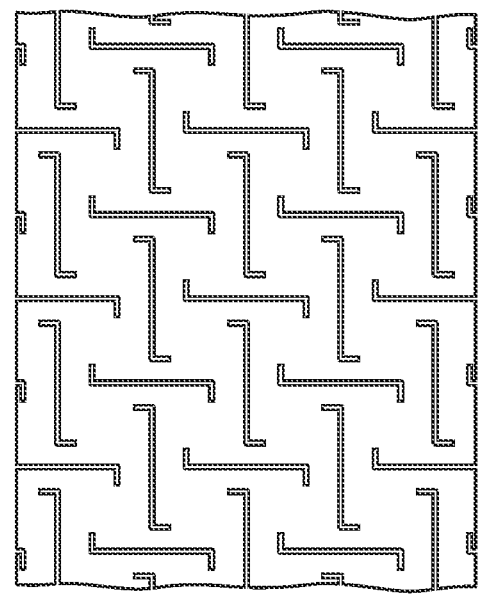
FIG. 9 shows a previously disclosed pattern of slit units used for comparison purposes.

Extension Displacement of Layer of Material with Slit Pattern Units of FIG. 9 Under Force along the Various Directions of in xy-Plane.

Test and Control samples were prepared and measured in accordance with the Stretchability Test$_{xy}$ to determine % difference in the extensibility along a given direction at a force F between samples with the slits of the present of the present invention (Test sample) and samples without slits (Control sample). The Test samples incorporated the slit pattern units of FIG. 9. The longitudinal, transverse and diagonal directions $D_{45}$ and $D'_{45}$ are illustrated as longitudinal, transverse and 45° diagonal directions (B, A, $D_{45}$ and $D'_{45}$) at FIG. 8. The data is summarized as extensibility or elongation data and the calculated % difference (i.e., $$\left(\left[\frac{\text{Test Sample at force } F}{\text{Control Sample at force } F} \times 100\right] - 100\right)$$

for the various directions of elongation or stretch in Tables 1-4 and 1a-4a, respectively.

TABLE 1

Extensibility (mm) in the Longitudinal Direction at Force F

| Force F (kgf) | 0.1 | 0.2 | 0.3 | 0.4 |
|---|---|---|---|---|
| Test Sample | 1.51 | 3.09 | 7.25 | 13.80 |
| Control Sample | 1.01 | 1.37 | 1.65 | 1.9 |

TABLE 1a

% Difference (versus Control) in Longitudinal Extensibility at Force F

| Force F (kgf) | 0.1 | 0.2 | 0.3 | 0.4 |
|---|---|---|---|---|
| Test Sample | 49% | 126% | 339% | 626% |
| Control Sample | — | — | — | — |

TABLE 2

Extensibility (mm) in the Transverse Direction at Force F

| Force F (kgf) | 0.1 | 0.2 | 0.3 | 0.4 |
|---|---|---|---|---|
| Test Sample | 2.10 | 4.68 | 14.92 | 21.96 |
| Control Sample | 1.46 | 2.2 | 2.92 | 3.63 |

TABLE 2a

% Difference (versus Control) in Transverse Extensibility at Force F

| Force F (kgf) | 0.1 | 0.2 | 0.3 | 0.4 |
|---|---|---|---|---|
| Test Sample | 44% | 112% | 412% | 504% |
| Control Sample | — | — | — | — |

TABLE 3

Extensibility (mm) in the Diagonal Direction $D'_{45}$ at Force F

| Force F (kgf) | 0.1 | 0.2 | 0.3 | 0.4 |
|---|---|---|---|---|
| Test Sample | 3.52 | 13.65 | 28.03 | 34.49 |
| Control Sample | 0.71 | 1.13 | 1.55 | 2.00 |

TABLE 3a

% Difference (versus Control) in Diagonal Direction $D'_{45}$ Extensibility at Force F

| Force F (kgf) | 0.1 | 0.2 | 0.3 | 0.4 |
|---|---|---|---|---|
| Test Sample | 395% | 1108% | 1708% | 1625% |
| Control Sample | — | — | — | — |

TABLE 4

Extensibility (mm) in the Diagonal Direction $D_{45}$ at Force F

| | Force F | | | |
|---|---|---|---|---|
| | 0.1 | 0.2 | 0.3 | 0.4 |
| Test Sample | 2.99 | 7.60 | 14.07 | 19.55 |
| Control Sample | 1.30 | 1.78 | 2.23 | 2.69 |

TABLE 4a

% Difference (versus Control) in Diagonal Direction $D_{45}$ Extensibility at Force F

| | Force F (kgf) | | | |
|---|---|---|---|---|
| | 0.1 | 0.2 | 0.3 | 0.4 |
| Test Sample | 130% | 327% | 531% | 627% |
| Control Sample | — | — | — | — |

Tables 1a, 2a, 3a and 4a show that the Slit Pattern Units of FIG. 9 provide some degree of the extensibility of the layer of material beyond the extensibility of that layer of material without any slits.

Inventive Example 2

Extension Displacement of Layer of Material with Slit Pattern Units of FIG. 2 Under Force along the Various Directions of in xy-Plane.

Test and Control samples were prepared and measured in accordance with the Stretchability Test$_{xy}$ to determine % difference in the extensibility along a given direction at a force F between samples with the slits of the present of the present invention (Test sample) and samples without slits (Control sample). The Test samples incorporated the slit pattern units of FIG. 2. The longitudinal, transverse and diagonal directions $D_{45}$ and $D'_{45}$ are illustrated as longitudinal, transverse and 45° diagonal directions (B, A, $D_{45}$ and $D'_{45}$) at FIG. 8. The data is summarized as extensibility or elongation data and the calculated % difference for the various directions of elongation or stretch in Tables 5-8 and 5a-8a, respectively.

TABLE 5

Extensibility (mm) in the Longitudinal Direction at Force F

| | Force F (kgf) | | | |
|---|---|---|---|---|
| | 0.1 | 0.2 | 0.3 | 0.4 |
| Test Sample | 6.07 | 13.34 | 19.13 | 23.94 |
| Control Sample | 1.01 | 1.37 | 1.65 | 1.9 |

TABLE 5a

% Difference (versus Control) in Longitudinal Extensibility at Force F

| | Force F (kgf) | | | |
|---|---|---|---|---|
| | 0.1 | 0.2 | 0.3 | 0.4 |
| Test Sample | 498% | 874% | 1059% | 1160% |
| Control Sample | — | — | — | — |

TABLE 6

Extensibility (mm) in the Transverse Direction at Force F

| | Force F (kgf) | | | |
|---|---|---|---|---|
| | 0.1 | 0.2 | 0.3 | 0.4 |
| Test Sample | 4.32 | 10.87 | 16.26 | 21.11 |
| Control Sample | 1.46 | 2.2 | 2.92 | 3.63 |

TABLE 6a

% Difference (versus Control) in Transverse Extensibility at Force F

| | Force F (kgf) | | | |
|---|---|---|---|---|
| | 0.1 | 0.2 | 0.3 | 0.4 |
| Test Sample | 196% | 394% | 458% | 481% |
| Control Sample | — | — | — | — |

TABLE 7

Extensibility (mm) in the Diagonal Direction $D'_{45}$ at Force F

| | Force F (kgf) | | | |
|---|---|---|---|---|
| | 0.1 | 0.2 | 0.3 | 0.4 |
| Test Sample | 17.78 | 30.53 | 38.17 | 45.3 |
| Control Sample | 0.71 | 1.13 | 1.55 | 2.00 |

TABLE 7a

% Difference (versus Control) in Diagonal Direction $D'_{45}$ Extensibility at Force F

| | Force F (kgf) | | | |
|---|---|---|---|---|
| | 0.1 | 0.2 | 0.3 | 0.4 |
| Test Sample | 2404% | 2602% | 2363% | 2165% |
| Control Sample | — | — | — | — |

TABLE 8

| | Extensibility (mm) in the Diagonal Direction $D_{45}$ at Force F | | | |
|---|---|---|---|---|
| | Force F | | | |
| | 0.1 | 0.2 | 0.3 | 0.4 |
| Test Sample | 1.55 | 2.62 | 3.88 | 5.37 |
| Control Sample | 1.30 | 1.78 | 2.23 | 2.69 |

TABLE 8a

| | % Difference (versus Control) in Diagonal Direction $D_{45}$ Extensibility at Force Force F (kgf) | | | |
|---|---|---|---|---|
| | 0.1 | 0.2 | 0.3 | 0.4 |
| Test Sample | 19% | 47% | 74% | 100% |
| Control Sample | — | — | — | — |

When compared with Tables 1a and 2a of Comparative Example 1, Tables 5a and 6a, respectively, of Inventive Example 2 show that the layer of material having the Slit Pattern Units of FIG. 2 provides greater extension in at least one of the longitudinal or transverse directions than the layer of material having the Slit Pattern Units of FIG. 9 at forces 0.1-0.4 kgf and in the other (or remaining) longitudinal or transverse direction at forces 0.1-0.3 kgf.

Additionally, Table 7a compared with Table 3a shows the following for the two patterns with respect to extensibility in at least one of the 45° diagonal directions:

Table 7a shows that the Slit Pattern Units of FIG. 2 provides greater extension in at least one of the 45° diagonal directions than the layer of material having the Slit Pattern Units of FIG. 9 at forces 0.1-0.4 (as shown in Table 3a); and Example 3

To compare the extensibility in the z-direction of the prepared Test and Control samples of the Slit Pattern Units of FIG. 2, Test and Control samples were prepared and measured at forces 0.1 kgf and 0.5 kgf in accordance with the Stretchability Test$_z$. The results are summarized in Tables 9 and 9a, respectively.

TABLE 9

| | z-Directional Extensibility (mm) at Force of 0.1 kgf | | | | | | | | | |
|---|---|---|---|---|---|---|---|---|---|---|
| | 1 | 2 | 3 | 4 | 5 | 6 | 8 | 10 | 15 | 20 |
| Test Sample | Yes | Yes | Yes | Yes | No | No | No | No | No | No |
| Control Sample | Yes | No | No | No | No | No | No | No | No | No |

Table 9 shows that the layer of material with Slit Pattern Units of FIG. 2 permits a greater degree of movement in the z direction (or along the z-axis) at a force of 0.1 kgf than the layer of material without any slits at the same force.

TABLE 9a

| | z-Directional Extensibility (mm) at Force of 0.5 kgf | | | | | | | | | |
|---|---|---|---|---|---|---|---|---|---|---|
| | 1 | 2 | 3 | 4 | 5 | 6 | 8 | 10 | 15 | 20 |
| Test Sample | Yes | Yes | Yes | Yes | Yes | Yes | Yes | No | No | No |
| Control Sample | Yes | Yes | Yes | No | No | No | No | No | No | No |

Table 9a shows that the layer of material with Slit Pattern Units of FIG. 2 permits a greater degree of movement in the z direction (or along the z-axis) at a force of 0.5 kgf than the layer of material without any slits at the same force.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined.

It is to be understood that at least some of the figures and descriptions of the invention have been simplified to focus on elements that are relevant for a clear understanding of the invention.

Further, to the extent that any method does not rely on the particular order of steps set forth herein, the particular order of the steps should not be construed as limitation on the claims. The claims directed to any such method of the present invention should not be limited to the performance of their steps in the order written, and one skilled in the art can readily appreciate that the steps may be varied and still remain within the spirit and scope of the present invention.

EMBODIMENTS OF THE PRESENT INVENTION

1. A dressing, comprising a layer of material, the layer comprising a plurality of material free regions wherein the material free regions are in the form of sigmoid pattern units, the sigmoidal patterns having dimensions and oriented and arranged such that the layer of material extends in at least one of the 45° diagonal directions at least about 425% more than the same layer of material without material free regions, as measured by the Stretchability Test$_{xy}$ described in the Specification, when applying a force of from about 0.1 kgf along such 45° diagonal direction of the layer of material.
2. The dressing of embodiment 1, wherein the material free regions are slits in the layer of material.
3. The dressing of embodiments 1 and/or 2, wherein the patterns are non-intersecting and arranged adjacent to one another to form one or more linear rows.
4. The dressing of any one or combination of embodiments 1-3, wherein the linear rows are parallel to each other.
5. The dressing of any one or combination of embodiments 1-4, wherein each sigmoidal pattern has a top and a bottom and further wherein the top and bottom of any sigmoidal pattern in a row is aligned with the top and bottom of the other similarly oriented sigmoidal patterns in that row.
6. The dressing of any one or combination of embodiments 1-5, wherein the sigmoidal patterns have a length l and, optionally. wherein the length l of at least one sigmoidal pattern is oriented perpendicular to the length l of an adjacent sigmoidal pattern.

7. The dressing of any one or combination of embodiments 1-6, wherein the lengths l of each sigmoidal pattern in a row is oriented perpendicular to the length l of its adjacent sigmoidal pattern in the row.

8. The dressing of any one or combination of embodiments 1-7, wherein the sigmoidal patterns have a width w and further wherein the length l of the sigmoidal pattern is from about 1 to about 6 times the width w of sigmoidal pattern.

9. The dressing of any one or combination of embodiments 1-8, wherein the surface density of pattern units per square inch of the surface of the layer of material is from about 10 pattern units/in$^2$ to about 14 pattern units/in$^2$ of the surface of the layer of material.

10. The dressing of any one or combination of embodiments 1-9, wherein the layer of material extends in at least one of the 45° diagonal directions at least about 1125% more than the same layer of material without material free regions, as measured by the Stretchability Test$_{xy}$ described in the Specification, when applying a force of from about 0.2 kgf along such 45° diagonal direction of the layer of material.

11. The dressing of any one or combination of embodiments 1-10, wherein the layer of material extends in at least one of the 45° diagonal directions at least about 1725% more than the same layer of material without material free regions, as measured by the Stretchability Test$_{xy}$ described in the Specification, when applying a force of from about 0.3 kgf along such 45° diagonal direction of the layer of material.

12. The dressing of any one or combination of embodiments 1-11, wherein the layer of material extends in at least one of the 45° diagonal directions at least about 1650% more than the same layer of material without material free regions, as measured by the Stretchability Test$_{xy}$ described in the Specification, when applying a force of from about 0.4 kgf along such 45° diagonal direction of the layer of material.

13. The dressing of any one or combination of embodiments 1-12, wherein the layer of material extends in at least one of the longitudinal or transverse directions at least about 100% more than the same layer of material without material free regions, as measured by the Stretchability Test$_{xy}$ described in the Specification, when applying a force of from about 0.1 kgf along such longitudinal or transverse direction of the layer of material.

14. The dressing of any one or combination of embodiments 1-13, wherein the layer of material extends in at least one of the longitudinal or transverse directions at least about 150% more than the same layer of material without material free regions, as measured by the Stretchability Test$_{xy}$ described in the Specification, when applying a force of from about 0.2 kgf along such longitudinal or transverse direction of the layer of material.

15. The dressing of any one or combination of embodiments 1-14, wherein the layer of material extends in at least one of the longitudinal or transverse directions at least about 425% more than the same layer of material without material free regions, as measured by the Stretchability Test$_{xy}$ described in the Specification, when applying a force of from about 0.3 kgf along such longitudinal or transverse direction of the layer of material.

16. The dressing of any one or combination of embodiments 13-15, wherein the layer of material extends in the other longitudinal or transverse direction at least about 75% more than the same layer of material without material free regions, as measured by the Stretchability Test$_{xy}$ described in the Specification, when applying a force of from about 0.1 kgf along such other longitudinal or transverse direction of the layer of material.

17. The dressing of any one or combination of embodiments 13-15, wherein the layer of material extends in the other longitudinal or transverse direction at least about 150% more than the same layer of material without material free regions, as measured by the Stretchability Test$_{xy}$ described in the Specification, when applying a force of from about 0.2 kgf along such other longitudinal or transverse direction of the layer of material.

18. The dressing of any one or combination of embodiments 1-17, wherein the layer of material extends in the z direction at least about 1 mm to about 8 mm away from the xy-plane of the layer of material, as measured by the Stretchability Test$_z$ described in the Specification, when applying a force of about 0.5 kgf along the z direction of the layer of material.

19. The dressing of any one or combination of embodiments 1-18, further comprising an adhesive disposed between the releasable layer and the layer of material.

20. The dressing of any one or combination of embodiments 1-19, wherein the releasable layer comprises polyethylene, polypropylene, kraft papers, polyester or composites thereof.

What is claimed is:

1. An adhesive bandage comprising:
    (a) a dressing comprising a layer of material comprising a laminate having a nonwoven layer comprising polyester fibers and a nonstick, high density polyethylene net, the layer of material having a plurality of material free regions, wherein:
        (i) the material free regions are in the form of curvilinear sigmoid pattern units, the curvilinear sigmoidal pattern units having dimensions and oriented and arranged in a regular array such that the layer of material has a Stretchability Testxy extension in at least one of a 45° diagonal direction of at least 1125% more than the same layer of material without material free regions when applying a force of from 0.2 kgf along such 45° diagonal direction of the layer of material; and
        (ii) the curvilinear sigmoidal pattern units have a width w and a length l, and further wherein the length l of the curvilinear sigmoidal pattern unit is from 1 to 6 times the width w of the curvilinear sigmoidal pattern unit; and
    (b) a backing layer comprising an elastomeric film having an adhesive disposed on a major surface thereof and being adhered to the nonwoven layer of the laminate; wherein, upon application of the adhesive bandage to a user's skin in a substantially unstressed condition, the dressing is capable of stretching with the skin during use to minimize detachment of the dressing therefrom.

2. The adhesive bandage of claim 1, wherein the material free regions are cuts or slits in the layer of material.

3. The adhesive bandage of claim 1, wherein the curvilinear sigmoidal pattern units are non-intersecting and arranged adjacent to one another to form one or more linear rows.

4. The adhesive bandage of claim 3, wherein the linear rows are parallel to each other.

5. The adhesive bandage of claim 1, wherein each curvilinear sigmoidal pattern unit has a top and further wherein the bottom of any curvilinear sigmoidal pattern unit in a row is aligned with the top and bottom of the other curvilinear sigmoidal pattern units in that row.

6. The adhesive bandage of claim 1, wherein the length/of at least one curvilinear sigmoidal pattern unit is oriented perpendicular to the length/of an adjacent curvilinear sigmoidal pattern unit.

7. The adhesive bandage of claim 6, wherein the length l of each curvilinear sigmoidal pattern unit in a row is oriented perpendicular to the length l of its adjacent curvilinear sigmoidal pattern unit in the row.

8. The adhesive bandage of claim 1, wherein the surface density of curvilinear sigmoidal pattern units per square inch of the surface of the layer of material is from 10 pattern units/in$^2$ to 14 pattern units/in$^2$ of the surface of the layer of material.

9. The adhesive bandage of claim 1, wherein the layer of material has a Stretchability Test$xy$ extension in at least one of the 45° diagonal directions of at least 1725% more than the same layer of material without material free regions, when applying a force of from 0.3 kgf along such 45° diagonal direction of the layer of material.

10. The adhesive bandage of claim 1, wherein the layer of material has a Stretchability Test$xy$ extension in at least one of the 45° diagonal directions of at least 1650% more than the same layer of material without material free regions, when applying a force of from 0.4 kgf along such 45° diagonal direction of the layer of material.

11. The adhesive bandage of claim 1, wherein the layer of material has a Stretchability Test$xy$ extension in at least one of the longitudinal or transverse directions of at least 100% more than the same layer of material without material free regions, when applying a force of from 0.1 kgf along such longitudinal or transverse direction of the layer of material.

12. The adhesive bandage of claim 1, wherein the layer of material has a Stretchability Test$xy$ extension in at least one of the longitudinal or transverse directions of at least 150% more than the same layer of material without material free regions, when applying a force of from 0.2 kgf along such longitudinal or transverse direction of the layer of material.

13. The adhesive bandage of claim 1, wherein the layer of material has a Stretchability Test$xy$ extension in at least one of the longitudinal or transverse directions of at least 425% more than the same layer of material without material free regions when applying a force of from 0.3 kgf along such longitudinal or transverse direction of the layer of material.

14. The adhesive bandage of claim 11, wherein the layer of material has a Stretchability Test$xy$ extension in the other longitudinal or transverse direction of at least 75% more than the same layer of material without material free regions when applying a force of from 0.1 kgf along such other longitudinal or transverse direction of the layer of material.

15. The adhesive bandage of claim 12, wherein the layer of material has a Stretchability Test$xy$ extension in the other longitudinal or transverse direction of at least 150% more than the same layer of material without material free regions when applying a force of from 0.2 kgf along such other longitudinal or transverse direction of the layer of material.

16. The adhesive bandage of claim 1, wherein the layer of material has a Stretchability Test$z$ extension of at least 1 mm to 8 mm away from the xy-plane of the layer of material when applying a force of 0.5 kgf along the z direction of the layer of material.

17. The adhesive bandage of claim 1 wherein the backing layer comprises a polyurethane film.

18. The adhesive bandage of claim 17 wherein the backing layer further comprises a woven fabric.

19. The adhesive bandage of claim 1 wherein the wherein the length l of the curvilinear sigmoidal pattern unit is from 2.5 to 6 times the width w of the curvilinear sigmoidal pattern unit.

* * * * *